US005633286A

United States Patent [19]

Chen

[11] Patent Number: 5,633,286
[45] Date of Patent: *May 27, 1997

[54] GELATINOUS ELASTOMER ARTICLES

[75] Inventor: John Y. Chen, Pacifica, Calif.

[73] Assignee: Applied Elastomerics, Inc., South San Francisco, Calif.

[*] Notice: The term of this patent shall not extend beyond the expiration date of Pat. No. 5,336,708.

[21] Appl. No.: 288,690

[22] Filed: Aug. 11, 1994

Related U.S. Application Data

[63] Continuation-in-part of PCT/US94/07314, Jun. 27, 1994, which is a continuation-in-part of PCT/US94/04278, Apr. 19, 1994, which is a continuation-in-part of Ser. No. 957,290, Oct. 6, 1992, Pat. No. 5,334,646, Ser. No. 152,734, Nov. 15, 1993, Pat. No. 5,624,294, Ser. No. 152,735, Nov. 15, 1993, Pat. No. 5,508,334, and Ser. No. 114,688, Aug. 30, 1993, Pat. No. 5,475,890, which is a continuation-in-part of Ser. No. 934,027, Aug. 24, 1992, Pat. No. 5,239,723, and Ser. No. 935,540, Aug. 24, 1992, Pat. No. 5,336,708, which is a continuation-in-part of Ser. No. 705,711, May 23, 1991, Pat. No. 5,262,468, Ser. No. 876,118, Apr. 29, 1992, Pat. No. 5,324,222, and Ser. No. 705,096, May 23, 1991, said Ser. No. 876,118, and Ser. No. 705,096, each is a continuation-in-part of Ser. No. 527,058, May 21, 1990, abandoned, said Ser. No. 705,711, and Ser. No. 527,058, each is a continuation-in-part of Ser. No. 211,426, Jun. 24, 1988, Pat. No. 5,153,254, which is a continuation-in-part of Ser. No. 921,752, Oct. 21, 1986, abandoned, which is a continuation-in-part of Ser. No. 572,172, Jan. 18, 1984, Pat. No. 4,618,213, which is a continuation-in-part of Ser. No. 458,703, Jan. 17, 1983, abandoned, which is a continuation-in-part of Ser. No. 134,977, Mar. 28, 1980, Pat. No. 4,369,284, which is a continuation-in-part of Ser. No. 916,731, Jun. 19, 1978, abandoned, which is a continuation-in-part of Ser. No. 815,315, Jul. 13, 1977, abandoned, which is a continuation-in-part of Ser. No. 778,343, Mar. 17, 1977, abandoned.

[51] Int. Cl.[6] .................. C08K 5/00; C08K 5/01; A42B 3/00; C08L 3/00

[52] U.S. Cl. .................. 524/474; 524/476; 524/490; 524/505; 525/95; 2/411; 5/632; 5/636; 5/640; 132/321; 135/68; 135/71; 135/72; 135/82; 297/391; 297/392; 297/394; 297/397

[58] Field of Search .................. 524/474, 490, 524/505, 476; 2/411; 5/632, 636, 640; 132/321; 135/68, 71, 72, 82; 297/391, 392, 394, 397, DIG. 1, DIG. 4; 521/148; 428/52; 525/95

[56] References Cited

U.S. PATENT DOCUMENTS

| 5,134,254 | 7/1992 | Chen | 524/505 |
|---|---|---|---|
| 5,135,978 | 8/1992 | Sasaki | 524/274 |
| 5,221,534 | 6/1993 | DesLauriers | 424/78.03 |
| 5,239,723 | 8/1993 | Chen | 15/104.002 |
| 5,262,468 | 11/1993 | Chen | 524/496 |
| 5,324,222 | 6/1994 | Chen | 446/34 |
| 5,334,646 | 8/1994 | Chen | 524/474 |
| 5,336,708 | 8/1994 | Chen | 524/474 |

*Primary Examiner*—Herbert J. Lilling

[57] ABSTRACT

Novel composites are formed from a low rigidity oriented and non-oriented gelatinous elastomer composition of poly (styrene-ethylene-butylene-styrene) or poly(styrene-ethylene-proplene-styrene) triblock copolymer and high levels of a plasticizing oil. The gelatinous elastomer composition is physically interlocked with an open cell sponge thereby displacing the air space within the sponge and the gel rigidity is found to be greater than about the sum of the combined rigidity of the gelatinous elastomer composition and sponge alone. The gelatinous elastomer composite exhibits a novel combination of properties including unexpectedly high elongation and tensile strength and excellent shape retention after extreme deformation under high-velocity impact and stress conditions. The gelatinous elastomer composites can be made firm or soft and flexible. These and other properties are particularly essential for the gelatinous elastomer composites to have utility as toys, therapeutic hand exercising grips, shock absorbers, acoustical isolators, vibration dampers, vibration isolators, wrappers, hand exercisers, crutch cushions, cervical pillows, bed wedge pillows, leg rest cushions, neck cushions, bed pads, elbow pads, dermal pads, wheelchair cushions, helmet liners, hot or cold compress pads, exercise weight belts, swabs, traction pads, splints, slings, rib supports, orthopedic shoe soles, brace cushions for the hand, wrist, finger, forearm, knee, leg, clavicle, shoulder, foot, ankle, neck, back, and the like.

8 Claims, 6 Drawing Sheets

| | |
|---|---|
| M1 | Fabric or Cloth |
| G | Gel |
| GM | Gel-Sponge or Gel-Foam |
| M2 | Foam or Sponge |
| M3 | Synthetic Resin or Plastic |
| M4 | Fibre |
| M5 | Concrete |
| M6 | Metal or Metal Sponge |
| M7 | Wood |
| M8 | Wire or Screening |
| M9 | Refractory Material |
| M10 | Other Material |

Figure 1

GELATINOUS ELASTOMER ARTICLES

REFERENCE TO RELATED APPLICATIONS AND PATENTS

This application is a CIP of PCT/US94/07314 filed Jun. 27, 1994 which is a CIP of PCT/US94/04278 filed Apr. 19, 1994 which is a CIP of Ser. No. 07/957,290 filed Oct. 6, 1992 now U.S. Pat. No. 5,334,646 and a CIP of Ser. No. 08/152,734 filed Nov. 15, 1993, now U.S. Pat. No. 5,624,294, and a CIP of Ser. No. 08/152,735 filed Nov. 15, 1993, now U.S. Pat. No. 5,508,334, and a CIP of Ser. No. 08/114,688 filed Aug. 30, 1993, now U.S. Pat. No. 5,475,890, which is a CIP of Ser. No. 07/934,027 filed Aug. 24, 1992 now U.S. Pat. No. 5,239,723 and a CIP of Ser. No. 07/935,540 filed Aug. 24, 1992 now U.S. Pat. No. 5,336,708 which is a CIP of Ser. No. 07/705,711 filed May 23, 1991 now U.S. Pat. No. 5,262,468 and a CIP of Ser. No. 07/876,118 filed Apr. 29, 1992 now U.S. Pat. No. 5,324,222 and a CIP of Ser. No. 07/705,096 filed May 23, 1991 said Ser. No. 07/876,118 and said Ser. No. 07/705,096 which are CIPs of Ser. No. 07/527,058 filed May 21, 1990 abandoned said Ser. No. 07/705,711 and said Ser. No. 07/527,058 which are CIPs of Ser. No. 211,426 filed Jun. 24, 1988, now U.S. Pat. No. 5,153,254, which is a CIP of Ser. No. 921,752 filed Oct. 21, 1986, now abandoned, which is a CIP of Ser. No. 572,172, filed Jan. 18, 1984 and issued as U.S. Pat. No. 4,618,213 on Oct. 21, 1986, which is a CIP of Ser. No. 458,703, filed Jan. 17, 1983, now abandoned, which is a CIP of Ser. No. 134,977, filed Mar. 28, 1980 and issued as U.S. Pat. No. 4,369,284 on Jan. 18, 1983, which in turn is a CIP of Ser. No. 916,731, filed Jun. 19, 1978, now abandoned, which is a CIP of Ser. No. 815,315, filed Jul. 13, 1977, now abandoned, which is a CIP of Ser. No. 778,343, filed Mar. 17, 1977, now abandoned. The subject matter contained in the related applications and patents are specifically incorporated herein by reference.

FIELD OF THE INVENTION

The present invention relates to useful gelatinous elastomer articles formed from a low rigidity gel.

BACKGROUND OF THE INVENTION

UK Patent No. 1,268,431 as well as U.S. Pat. No. 3,676,387 teach forming gel articles having odd or intricate shapes, insoles for boots, ski boot liners, helmet liners, and very flexible exceptionally low modulus material. The gels can be covered with protective skins of elastomeric film or fabric if desired in special applications. Examples given in the patents include coating polyester film with a styrene-isoprene-styrene block copolymer gel and laminating fabric with a styrene-butadine-styrene block copolymer gel.

SUMMARY OF THE INVENTION

The embodiments of the composite articles of the invention comprises a thermoplastic, heat formable and heat reversible gelatinous elastomer composition, G, which is physically interlocked with a selected material Mn, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed from the combination GnMn, GnMnGn, MnGnMn, MnGnGn, GnGnMn, MnGnMn, MnGnGnMn, MnGnGnMn, GnMnGnMn, MnGnGnGn, MnMnMnGn, MnGnMnMn, MnMnGnMnMn, MnGnMnGn, GnMnGnGn, GnMnGnGn, GnGnMnMn, GnGnMnGnMn, GnGnMnGn, GnGnGnMnGnGn, GnMnGnMnMn, GnMnGnMnGn, GnMnGnGnMn, GnGnGnMn, GnGnGnMnGn, GnGnGnMn, GnGnGnMnMn, GnGnGnGnMn, MnGnGnMnGn, MnGnMnGnMn, GnGnMnmnMn, GnMnMnGnMn, MnGnMnGnMnGn, GnGnMnMnGn, GnGnMnGnMnGn, GnMnGnMnGnMn, GnMnGnMnGnMn, MnGnGnMnGnMn, GnGnMnMnGnGn, MnMnGnGnMnMn, MnGnGnMnGnMn, MnGnGnMnGnGn.

GnGnMnGnMnGn, GnMnGnMnGn, MnMnMnGnMnMn, MnGn MnGnMnGnGnMn, GnMnGnMnGnMnGn, MnGnMnGnMnMnGn, GnMnMnGnMnMnGn, MnGnGnMnGnGnMn, GnMnGnMnGnMnGn, MnGnMnMnGnGnMn, GnGnMnMnGnGnMnMn, GnGnMnGnGnMnGn, MnGnGnMnGnMn,GnMnGnGnMnGnMn, GnGnMnGnMnGnMnGn, GnMnGnMnGnMnGn, GnGnMnGnMnGnGn, GnMnMnMnGn, MnMnMnGnMnGnMnMnMn . MnMnMnGnMnGnMnMnMn . MnMnMnGnMnMnMnGnMnMnMn . GnMnGnMnGnMnGnMnGn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different gel rigidity; said triblock copolymer is a linear, multi-arm, branched, or star shaped copolymer of the general configuration poly(styrene-ethylene-butylene-styrene), poly(styrene-ethylene-propylene-styrene), or a mixture of therof and optionally in combination with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene), low viscosity poly(styrene-ethylene-propylene-styrene), low viscosity poly(styrene-ethylene-butylene-styrene), poly(styrene-ethylene-butylene), polystyrene, polybutylene, poly(ethylene-propylene), poly(ethylene-butylene), polyproplyene, or polyethylene, wherein said selected copolymer is a linear, branched, multiarm, or star shaped copolymer.

The various aspects and advantages of the invention will become apparent to those skilled in the art upon consideration of the accompanying disclosure and the drawings.

DESCRIPTION OF THE DRAWINGS

FIG. 1. Representative components materials of composites forming useful articles of the invention.

DESCRIPTION OF THE PREFERRED EMBODIMENTS

Figure 2:
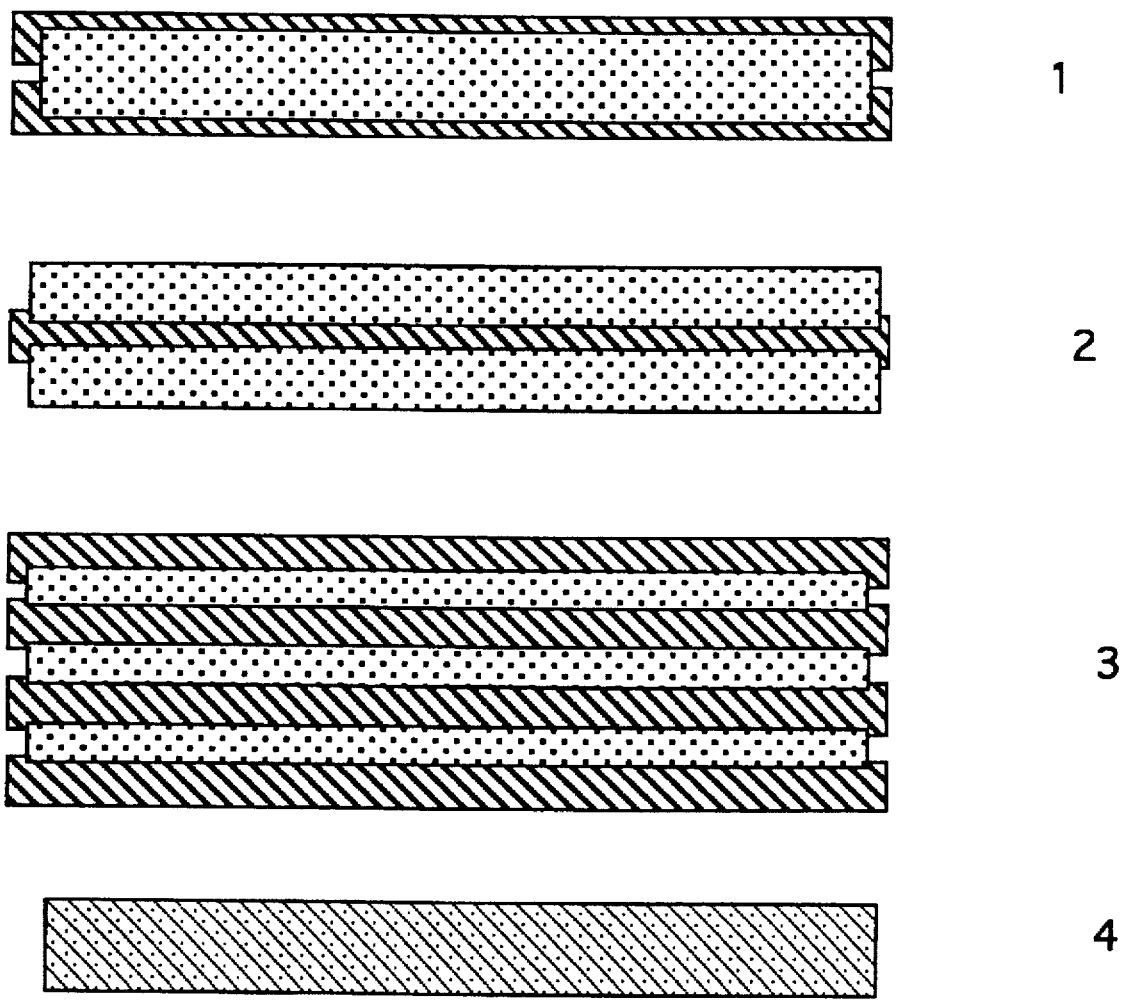
FIGS. 2a–2d. Representative sectional view of composite articles of the invention (FIG. 2a. = MGM, FIG. 2b. = GMG, FIG. 2c. = MGMGMGM, FIG. 2d. = foam entirely interlocked with composition).

Applicant's related parent application Ser. No. 921,752, filed Oct. 21, 1986, and application Ser. No. 211,426, filed Jun. 24, 1988 describe various useful gel articles and forming gel-foam or gel-sponge composite articles. The gelatinous elastomer composition of the present invention have various novel properties which makes them useful, for example, as hand grips sold under the trademark RECOVERY®. The hand grips can distribute the gripping force over the entire contact surface of the hand without high stress concentrations. The grips are ideal for exercises requiring extreme softness and adequate distribution of the gripping force approximating that of hydrostatic pressure. Hand grips having greater rigidities are sold under the trademark STAMINA™ and ENDURANCE™. These grips require an increase in the the triblock copolymer component of the overall gelatinous elastomer composition.

The gel rigidity of the gelatinous elastomer and foam composites (gel-foam composite) are found to be greater than the sum of the combined rigidity of the gelatinous elastomer composition and foam alone. This and other properties of the gel-foam composites are particularly essential for the gel-foam composites to be formed into useful articles having utility as toys, therapeutic hand exercising grips, shock absorbers, acoustical isolators, vibration dampers, vibration isolators, wrappers, hand exercisers, crutch cushions, cervical pillows, bed wedge pillows, leg rest cushions, neck cushions, bed pads, elbow pads, dermal pads, wheelchair cushions, helmet liners, hot or cold compress pads, exercise weight belts, swabs, traction pads, splints, slings, rib supports, orthopedic shoe soles, brace cushions for the hand, wrist, finger, forearm, knee, leg, clavicle, shoulder, foot, ankle, neck, back, and the like.

A further embodiment of the invention is to provide oriented gels with improved high strength alignment properties as evidenced by optical techniques such as viewing oriented gel in plane-polarized light. Oriented gels exhibit birefringence in the relaxed unextended state. Oriented gels with improved strength are suitable for use as dental floss since they do not break as easly as un-oriented gels of the same rigidity.

Oriented gels aliened by controlled stretching during the gel's transition from a heated, non melting, non flowing state and the cooled solid gel state produces strong gels which are found to have greater tensile strength than gels of the same rigidity which have not been stretched to a selected degree during its heating and cooling histories. Gels which are selectively stretched during its (non melt flowing) heated state and rapidly coolled by flowing air, cold liquid bath or in contact with a cool surface exhibit optical birefringence when viewed under plane-polarized light. The degree of streaching during the gels cooling history from the heated state can vary. Stretching of at least about 50% to more than about 1000% are of advantage to produce birefrigence and stronger gels. Birefrigence is not observed in relaxed gels which do not undergo stretching during its heating and cooling histories. Slight to very strong birefringence are observed in rleaxed gels which are stretched during its heating and cooling histories. It is evident that stressing the gel during its cooling history as it cools from the heated state produce unexpected stronger oriented gels. We therefore consider oriented gels to be a new and novel composition physically different from the less stronger gels formed without stressing during the gels cooling history. Oriented gels may be formed in combination with various substrates such as described below. In past situations where in order to obatin stronger gel strength, gels with higher rigidities and lower plasticizer content must be used, it is now possible to make a oriented gel with the same plasticizer content having a higher useful gel strength.

In situations where the deformation and/or dynamic motion (as a result of pressure, stress or shear forces) of an gelatinous elastomer article requires a small step-wise or large increase or decrease in rigidities over a large or specific isolated areas of an internal or external surface area of an article, various gel rigidities can be laminated together to produce the required effect. Manufacturing such articles can be complicated and may require a great deal of time.

The lamination of varying rigidities to produce an article (e.g. crutch cushions, cervical pillows, bed wedge pillows, leg rest cushions, neck cushions, bed pads, elbow pads, dermal pads, wheelchair cushions, rib supports, orthopedic shoe soles, brice cushions, etc.) can be eliminated by using of one or more open cell foams or sponges in combination with a selected rigidity of the gelatinous elastomer composition.

Gelatinous elastomer compositions with different rigidities can also be used in combination with such foams or sponges. Likewise, foam with different pore size can be used to form the composite articles of the invention depending on use and function of the resulting article. The effect of different pore size on the resultant rigidity of the final composite can be substantial. For example, increasing the pore number (ppi = pores per inch) will result in an increase of the composite article's rigidity and decreasing the pore number will lower the rigidity of the final composite article. Thickness of the foam can also be a factor on other properties of the composite article. A different effect can be achieved with the use of multiple layers of foam or other materials, such as fabric-gel-fabric-gel-fabric.

The gelatinous elastomer composite articles can be formed in combination with other materials, such as open cell foam and sponges, other polymeric or elastomeric (Kraton) materials, porous materials, multi-layered coatings, signal layered, composite layered materials. The opened cell sponge when dipped into the instant composition will form an interpenetrating physical networks (interlocking of gel and foam (FIG. 2d).

Other materials (FIG. 1.) can be utilized to form the composite articles include: GMG (FIG. 2b), MGM (FIG. 2a), $MG_1G_2M$, $M_1M_2G_1G_2$, $M_2M_1G_1G_2$, $G_1MG_1G_2$, $MG1G_2$, $G_1G_2$ M, $G_2$ $G_1M$, $GM_1M_2$ G, $G_1M_1G_2$ $M_2$ $M_1$, $M_1GM_2GM_3GM_4$ (FIG. 2c), etc. where G = gel and M = material. The subscript 1, 2, 3, 4, etc., are different and is represented by n which is a positive number, when n is a subscript of M, n may be the same or different material and when n is a subscript of G, n can be the same or different rigidity, oriented or non-oriented gel or the same or different gel material composition. The material (M) suitable for forming composite articles with the gelatinous elastomer compositions can include foam, plastic, fabric, metal, concrete, wood, wire screen, refractory material, glass, synthetic resin, synthetic fibers, and the like. Sandwiches of gel/material (i.e. gel-material-gel (FIG. 2b) or material-gel-material (FIG. 2a), etc.) are ideal for use as shock absorbers, acoustical isolators, vibration dampers, vibration isolators, and wrappers. For example the vibration isolators can be use under research microscopes, office equipment, tables, and the like to remove background vibrations.

The compositions of the invention can be casted unto various substrates, such as open cell materials, metals, ceramics, glasses, plastics, etc. Useful open-cell plastics include: polyamides, polyimides, polyesters, polyisocyanurates, polyisocyanates, polyurethanes, poly (vinyl alcohol), etc. Open-celled Plastic (sponges) suitable for use with the compositions of the invention are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

Triblock copolymer gels especially suitable for use in forming the gel components of the composites of the invention include: SEBS gels; examples include: (a) Kraton G 1651, G 1654X gels; (b) Kraton G 4600 gels; (c) Kraton G 4609 gels; other less suitable SEBS oil gels: examples include: (d) Tuftec H 1051 gels; (e) Tuftec H 1041 gels; (f) Tuftec H 1052 gels. Gels made from blends (polyblends) of (a)–(f) with other polymers and copolymers include: SEBS-SBS gels; SEBS-SIS gels; SEBS-(SEP) gels; SEBS-(SB)n gels; SEBS-(SEB)n gels; SEBS-(SEP)n gels; SEBS-(SI)n gels; SEBS-(SI) multiarm gels; SEBS-branched copolymers gels; SEBS-star shaped copolymer gels; gels made from blends of (a)–(f) with other homopolymers include: SEBS/polystrene gels; SEBS/polybutylene gels; SEBS/polyethylene gels; SEBS/polypropoylene gels. Other suitable thermoplastic elastomers in blends suitable for making gels include SEP/SEBS oil gels, SEP/SEPS oil gels, SEP/SEPS/SEB oil gels, SEPS/SEBS/SEP oil gels, SEB/SEBS, EB-EP/SEBS, SEBS/EB, SEBS/EP, SEPS/SEB, etc.

The following commercial elastomers can be formed with oil and in combination with other polymers into suitable gels for use in making the gel components of the composites of the invention: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158, D4240, G1650, G1652, G1657, G1701X, G1702X, G1726X, G1750X, G1765X, FG1901X, FG1921X, D2103, D2109, D2122X, D3202, D3204, D3226, D5298, D5999X, D7340, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940; Kuraray's SEP/SEPS/SEEPS: Nos. 1001(SEP), 2002(SEPS), 2003(SEPS), 2023(SEPS), 2043(SEPS), 2063 (SEPS), 2005(SEPS), 2006(SEPS), 1050(SEP), 2103 (SEPS), 2104(SEPS), 2105(SEPS), and 4055(SEEPS) manufactured by Kuraray Co., Ltd., wherein SEP is made from hydrogentaed styrene isoprene di-block copolymer (SI), SEPS is made from hydrogentaed styrene isoprene triblock copolymer(SIS), and SEEPS is made from hydrogenated styrene isoprene/butadiene block copolymer or more specifically made from hydrogenated styrene block polymer with 2-methyl-1,3-butadiene and 1,3-butadiene.

The most preferred gels forming the composites of the invention comprise a high viscosity triblock copolymers which have the more general configuration A-B-A wherein each A is a crystalline polymer end block segment of polystyrene; and B is a elastomeric polymer center block segment of poly(ethylene-butylene). The poly(ethylene-butylene) and polystyrene portions are incompatible and form a two-phase system consisting of sub-micron domains of glassy polystyrene interconnected by flexible poly (ethylene-butylene) chains. These domains serve to crosslink and reinforce the structure. This physical elastomeric network structure is reversible, and heating the polymer above the softening point of polystyrene temporarily disrupt the structure, which can be restored by lowering the temperature. This also applies to high viscosity poly (styrene-ethylene-propylene-styrene) triblick copolymers. Most recent reviews of triblock copolymers are found in the "ENCYCLOPEDIA OF POLYMER SCIENCE AND ENGINEERING", Volume 2 and 5, 1987–1988; "Thermoplastic Elastomers", MODERN PLASTIC ENCYCLOPEDIA, 1989; and Walker, B. M., Ed., et al., HANDBOOK OF THERMOPLASTIC ELASTOMERS, Van Nostrand Reinhold Co., 2nd Edition 1988. There publications are incorporated herein by reference).

The especially suitable gels can be prepared by melt blending an admixture comprising: (A) 100 parts by weight of a high viscosity triblock copolymer of the general configurations poly(styrene-ethylene-butylene-styrene) or poly (styrene-ethylene-propylene-styrene) (herein referred to as "SEBS" or "SEPS") where said triblock copolymer is characterized as having a Brookfield Viscosity of a 20 weight percent solids solution of said triblock copolymer in toluene at 25° C. of about 1,800 cps and higher. (B) from about 200 to about 1,300 parts by weight of an plasticizing oil.

Less typically, the Brookfield Viscosity values of (A) can range from about 1,800 cps to about 30,000 cps or higher. The proportion of hydrocarbon plasticizing oil in (B) is more preferably from about 250 to about 1,200 parts per 100 parts of the triblock copolymer.

The high viscosity triblock copolymer of the invention can have a broad range of styrene end block to ethylene and butylene center block ratio of approximately about 20:80 or less to about 40:60 or higher. Examples of high viscosity triblock copolymers that can be utilized to achieve one or more of the novel properties of the present invention are styrene-ethylene-butylene-styrene block copolymers (SEBS) available from Shell Chemical Company and Pecten Chemical Company (divisions of Shell Oil Company) under trade designations Kraton G 1651, Kraton G 1654X, Kraton G 4600, Kraton G 4609 and the like. Other grades of (SEBS) polymers can also be utilized in the present invention provided such SEBS polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene weight ratios for these Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values.

The styrene to ethylene and butylene weight ratio of SEBS useful in forming the bodies 2 can range from lower than about 20:80 to above about 40:60. More specifically, the values can be 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and etc. Other ratio values of less than 19:81 or higher than 51:49 are also possible. Shell Technical Bulletin SC:1393–92 gives solution viscosity as measured with a Brookfield model RVT viscometer at 25° C. for Kraton G 1654X at 10% weight in toluene of approximately 400 cps and at 15% weight in toluene of approximately 5,600 cps. Broadly, the styrene end block to ethylene and butylene center block ratio of the triblock copolymers of the invention is about 20:80 to about 40:60, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and most preferably about 33:67. In accordance with the present invention, triblock copolymers such as Kraton G 1654X having ratios of 31:69 or higher can be used and do exhibit some very similar physical properties in many respects to Kraton G 1651 while Kraton G 1654X with ratios below 31:69 may also be use, but they are less preferred due to their decrease in the desirable properties of the final gel. Various triblock copolymers of the gels forming the humdingers of the invention can be blended so as to produce a blend of varying ratios of triblock copolymers as desired.

Examples of moderate to high viscosity SEPS triblock and S-E-EP-S block copolymers includes Kuraray's 2006 4055 which exhibits a solution viscosities at 10 weight %, 30° C. of about 7.1 and 59 respectively and styrene contents by weight of about 35% and 30% respectively.

Examples of representative commercially oils include Amoco® polybutenes, hydrogenated polybutenes and polybutenes with epoxide functionality at one end of the polybutene polymer: Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27–37 cst @ 100° F. Viscosity), H-300E (635–690 cst @ 210° F. of Viscosity), Actipol E6 (365 Mn), E16 (973 Mn), E23 (1433 Mn) and the like. Example of various commercially oils include: ARCO Prime (55, 70, 90, 200, 350, 400 and the like), Duraprime and Tufflo oils (6006, 6016, 6016M, 6026, 6036, 6056, 6206, etc), other white mineral oils include: Bayol, Bernol, American, Blandol, Drakeol, Ervol, Gloria, Kaydol, Litetek, Lyondell (Duraprime 55, 70, 90, 200, 350, 400, etc), Marcol, Parol, Peneteck, Primol, Protol, Sonrex, and the like.

Generally, plasticizing oils with average molecular weights less than about 200 and greater than about 700 may also be used (e.g. H-300 (1290 Mn)).

Other polymers and copolymers (in major or minor amounts) can be melt blended with the SEBS as mentioned above without substantially decreasing the desired properties. Such polymers may also be utilized in one or more combinations of the composits of the invention; these include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, (SEPS) styrene-ethylene-propylene-styrene block copolymers, (SB)n styrene-butadiend and (SEB)n, (SEBS)n, (SEP)n, (SI)n styrene-isoprene multi-arm, branched, and star shaped copolymers and the like. Still, other homopolymers can be utilized in minor amounts; these include: polystyrene, polybutylene, polyethylene, polypropoylene and the like.

Gels having gel rigidities of from less than about 20 gram Bloom to about 800 gram Bloom and higher are especially advantageous and suitable for forming the composits of the invention, typically 200 gram Bloom to about 700 gram Bloom.

As used herein, the term "gel rigidity" in gram Bloom is determined by the gram weight required to depress a gel a distance of 4 mm with a piston having a cross-sectional area of 1 square centimeter at 23° C.

Gels less suitable and less advantageous for use in the present invention include oil gels as described in PCT Publications WO88/00603; WO9/305113; and WO91/05014.

Plasticizers particularly preferred for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

The gel utilized for the gel composits can also contain useful amounts of conventionally employed additives such as stabilizers, antioxidants, antiblocking agents, colorants, fragrances, flame retardants, other polymers in minor amounts and the like to an extend not affecting or substantially decreasing the desired properties of the present invention.

Additives useful in the gel of the present invention include: tetrakis[methylene 3,-(3'5'-di-tertbutyl-4"-hydroxyphenyl) propionate] methane, octadecyl 3-(3",5"-di-tert-butyl-4"-hydroxyphenyl) propionate, distearyl-pentaerythritol-diproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl] benzene), 4,4"-methylenebis(2,6-di-tert-butylphenol), steraric acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, calcium sterate, other metal sterates, waxes (e.g. polyethylene, polypropylene, microcrystalline, carnauba, paraffin, montan, candelilla, beeswax, ozokerite, ceresine, and the like). The gel can also contain metallic pigments (aluminum and brass flakes), TiO2, mica, fluorescent dyes and pigments, phosphorescent pigments, aluminatrihydrate, antimony oxide, iron oxides (Fe304, -Fe203, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on Magnetic Materials, Publication NMAB-426, National Academy Press (1985) is incorporated herein by reference.

The gels of the composites of the invention may be made non-adhearing, non-sticking, non-tacky by incorporating an advantage amount of stearic acid (octadecanoic acid) and metal stearates (e.g., calcium stearate, magnesium sterate, zinc stearate, etc.).

An advantage of making non-sticking, non-tacky gels is the use of waxes, steraric acid and waxes, metal sterate and waxes, metal sterate and steraric acid. The use of steraric acid alone do not reduce tack. The amount of steraric acid is also important. The ratio of 200 grams steraric acid to 2,000 gram of SEBS (a ratio of 0.1) will result in spotted tack reduction on the surface of the gel. A ratio of 250 to 2,000 will result in spotted crystalized regions on the surface of the gel or spotted tack reduction. A ratio of 300 to 2,000 will result in complete tack reduction with large crystallized regions on the surface of the gel. When microcrystalline waxes are incorporated together with steraric acid, the crystalization of steraric acid completely disapears from the surface of the gel. For example excellent result is achieved with 200 grams of steraric acid, 150 grams of microcrystalline wax and 2,000 grams of SEBS. The same excellent result is achieved when SEBS is adjusted to 3,000 grams, 4,000 grams, etc. The same result is achieved with SEPS.

The compositions of the present invention are prepared by blending together the components including other additives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amount of SEBS used. These components blend easily in the melt and a heated vessel equipped with a stirrer is all that is required. As an example, small batches can be easily blended in a test tube using a glass stirring rod for mixing. While conventional large vessels with pressure and/or vacuum means can be utilized in forming large batches of the instant compositions in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than about 10 rpm to about 40 rpm or higher.

While preferred components and formulation ranges have been disclosed herein, persons of skill in the art can extend these ranges using appropriate material according to the principles discussed herein. All such variations and deviations which rely on the teachings through which the present invention has advanced the art are considered to be within the spirit and scope of the present invention.

The instant composition is excellent for cast moulding and the moulded products have various excellent characteristics which cannot be anticipated form the properties of the raw components. Other conventional methods of forming the composition can be utilized.

The gelatinous elastomer composition of the invention is excellent for forming the gelatinous elastomer composite articles of the invention. The gelatinous elastomer composite articles can be formed by blending, melting, dipping, casting, injection molding, extruding and other conventional methods. For example, a foam of a preselected pore size can be placed in a mold cavity and a preselected amount of a preselected rigidity of gelatinous elastomer composition is then injected into the mold. The mold is allow to cool to room temperature and the article removed. A preselected rigidity of molten gelatinous elastomer composition can be cast directly onto a section of open cell foam to form the composite article. Likewise, an article of foam can be dipped into a preselected rigidity of molten gelatinous elastomer composition and re-dipped into the same or different composition of a different rigidity. The shaped composite article of the invention can be conventionally covered with protective skins of elastomeric film, fabric or both as needed.

The composition can also be remelted in any suitable hot melt applicator for hot dipping, extrusion, sputtering, or spraying on to the foams or sponges so as to form the gelatinous elastomer composite articles of the invention. The basis of this invention resides in the fact that a high viscosity poly(styrene-ethylene-butylene-styrene) triblock copolymer having styrene end block to ethylene and butylene center block ratio preferably within the contemplated range of from about 20:80 to about 40:60, more preferably from between about 31:69 to about 40:60 when blended in the melt with an appropriate amount of plasticizing oil makes possible the attainment of gelatinous elastomer compositions having a desirable combination of physical and mechanical properties, notably high elongation at break of at least 1,600%, ultimate tensile strength of about at least $8\times10^5$ dyne/cm$^2$, low elongation set at break of substantially not greater than about 2%, tear resistance of at least $5\times10^5$ dyne/cm$^2$, substantially about 100% snap back when extended to 1,200% elongation, and a gel rigidity of substantially not greater than about 700 gram Bloom. It should be noted that when the ratio falls below 31:69, various properties such as elongation, tensile strength, tear resistance and the like can decrease while retaining other desired properties, such as gel rigidity, flexibility, elastic memory.

More specifically, the gelatinous composition of the present invention exhibit one or more of the following properties. These are: (1) tensile strength of about $8\times10^5$ dyne/cm$^2$ to about $10^7$ dyne/cm$^2$; (2) elongation of about 1,600% to about 3,000% and higher; (3) elasticity modulus of about $10^4$ dyne/cm$^2$ to about $10^6$ dyne/cm$^2$; (4) shear modulus of about $10^4$ dyne/cm$^2$ to about $10^6$ dyne/cm$^2$ as measured with a 1, 2, and 3 kilogram load at 23° C.; (5) gel rigidity of about 20 gram Bloom or lower to about 800 gram Bloom as measured by the gram weight required to depress a gel a distance of 4 mm with a piston having a cross-sectional area of 1 square cm at 23° C.; (6) tear propagation resistance of at least about $5\times10^5$ dyne/cm$^2$; (7) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The gelatinous elastomer articles moulded from the instant compositions have various additional important advantages in that they do not crack, creep, tear, crack, or rupture in flextural, tension, compression, or other deforming conditions of normal use; but rather the moulded articles made from the instant composition possess the intrinsic properties of elastic memory enabling the articles to recover and retain its original moulded shape after many extreme deformation cycles as compared to prior art triblock copolymer oil-extended compositions. In applications where low rigidity, high elongation, good compression set and excellent tensile strength are important, the instant compositions would be preferred.

The gelatinous elastomer compositions of the present invention are useful in low frequency vibration applications, such as viscoelastic layers in constrained-layer damping of mechanical structures and goods, as viscoelastic layers used in laminates for isolation of acoustical and mechanical noise, as antivibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components. The compositions are also useful as moulded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. The compositions are also useful for forming various shaped articles for use as novel amusement toys. The compositions of the invention are useful as novel reusable lint removers for cleaning the computer mouse, computer and typewriter keyboards, camera lenses, LP records, various hard-to-clean corners of a car interior, and other nooks and crannies on the surface or inside buildings, houses, schools, ships, offices, and etc.

As an example of the versatility of use of the instant composition and composite articles formed therefrom, a hand exerciser can be made in any shape so long as it is suitable for use as a hand exerciser: a sphere shape, a cube shape, a rectangular shape, etc. Likewise, a wheelchair cushion can be made from the composition in almost any shape so long as it meets the needs of the user of the cushion. The same applies for brace cushions for the hand, wrist, finger, forearm, knee, leg, etc.

The instant compositions can be formed in any shape; the original shape can be deformed into another shape (to contact a regular or irregular surface) by pressure and upon removal of the applied pressure, the composition in the deformed shape will recover back to its original shape.

Generally the molten gelatinous elastomer composition will adhere sufficiently to certain plastics (e.g. acrylic, ethylene copolymers, nylon, polybutylene, polycarbonate, polystyrene, polyester, polyethylene, polypropylene, styrene copolymers, and the like) provided the temperature of the molten gelatinous elastomer composition is sufficient high to fuse or nearly fuse with the plastic. In order to obtain sufficient adhesion to glass, ceramics, or certain metals, sufficient temperature is also required (e.g. above 250° F.). Commercial resins which can aid in adhesion to materials (plastics, glass, and metals) may be added in minor amounts to the gelatinous elastomer composition, these resins include: Super Sta-tac, Nevtac, Piccotac, Escorez, Wingtack, Hercotac, Betaprene, Zonarez, Nirez, Piccolyte, Sylvatac, Foral, Pentalyn, Arkon P, Regalrez, Cumar LX, Picco 6000, Nevchem, Piccotex, Kristalex, Piccolastic, LX1035, and the like.

The invention is further illustrated by means of the following illustrative embodiments, which are given for purpose of illustration only and are not meant to limit the invention to the particular components and amounts disclosed.

EXAMPLE I

A comparison was made between a low viscosity poly (styrene-ethylene-butylene-styrene) triblock copolymer having styrene end block to ethylene and butylene center block ratio below the range between 31:69 to 40:60 and a high viscosity poly(styrene-ethylene-butylene-styrene) triblock copolymer of the invention. Three different triblock copolymers were melt blended separately with a paraffinic white petroleum oil. Table I below shows the physical properties obtain with respect to each of the different viscosity and styrene to ethylene and butylene ratio triblock copolymer oil-blends tested.

The properties were measured as follows: Tear Propagation (ASTM D 19938 modified), Cracking (ASTM D 518 Method B modified), Tensile Strength (ASTM D 412 modified), Ultimate elongation (ASTM D 412 modified), Tensile Set (ASTM D 412 Modified), Compression Set (ASTM D 395 modified), Snap Back, and Hand Kneading (60 seconds).

TABLE I

| Formulation S/EB Ratio[1] | Weight Parts | | |
|---|---|---|---|
| | A | B | C |
| SEBS[2] 28:72 | 100 | | |
| SEBS[3] 29:71 | | 100 | |
| SEBS[4] 33:67 | | | 100 |
| Paraffinic oil[5] | 400 | 400 | 400 |
| Stabilizer[6] | 2.5 | 2.5 | 2.5 |
| Breaking strength[7], dyne/cm$^2$ | $4 \times 10^5$ | $4 \times 10^5$ | $4 \times 10^6$ |
| Tear propagation[8], dyne/cm$^2$ | $8 \times 10^4$ | $7 \times 10^4$ | $1 \times 10^6$ |
| Compression set[10] at 24 hours | 81%(R) | 77%(R) | 0.0% |
| Rigidity, gram Bloom | 1,536 | 1,520 | 360 |

[1]Styrene to ethylene and butylene ratio
[2]Shell Kraton G1650 having a Brookfield viscosity of 1,500 cps as measured for a 20% weight solids solution in toluene at 25° C.
[3]Shell Kraton G 1652 having a Brookfield viscosity of 550 cps as measured for a 20% weight solids solution in toluene at 25° C.
[4]Shell Kraton G 1651 having a Brookfield viscosity of 2,000 cps as measured for a 20% weight solids solution in toluene at 25° C.
[5]ARCO prime 200,
[6]Irganox 1010,
[7]ASTM D 412 modified,
[8]ASTM D 1938 modified,
[9]ASTM D 412 modified,
[10]ASTM D 2395 modified,
[R]ruptured completely The results of Table I show drastically unacceptable poor properties of low viscosity triblock copolymers having styrene to ethylene and butylene ratios which are below the contemplated range of the instant invention.

EXAMPLE II

One hundred parts by weight of a high viscosity poly (styrene-ethylene-butylene-styrene) triblock copolymer (Shell Kraton G 1651) having a styrene end block to ethylene and butylene center block ratio of about 33:67 with 0.1 parts by weight of a stabilizer (Irrganox 1010) was melt blended with various quantities of a naphthenic oil (ARCO Tufflo 6024). Samples having the dimensions of 5 cm × 5 cm × 3 cm were cut and measured for gel rigidity on a modified Bloom gelometer as determined by the gram weight required to depress the gel a distance of 4 mm with a piston having a cross-sectional area of 1 cm$^2$. The average gel rigidity values with respect to various oil concentrations are set forth in Table II below.

TABLE II

| Oil per 100 parts of Triblock copolymer | Gel Rigidity, gram Bloom |
|---|---|
| 360 | 500 |
| 463 | 348 |
| 520 | 280 |
| 615 | 240 |
| 635 | 220 |
| 710 | 172 |
| 838 | 135 |
| 1,587 | 54 |

EXAMPLE III

Example II was repeated except about 980 parts oil was used and the gel rigidity found to about 101 gram Bloom. Other properties measured were: tensile strength at break about $4.4 \times 10^6$ dyne/cm2, elongation at break about 2,4470%, elasticity modulus about $3.5 \times 10^4$ dyne/cm2, and shear modulus about $3.7 \times 10^4$ dyne/cm2. The tensile strength, elongation, elasticity modulus were measured with cross-head separation speed of 25 cm/minute at room temperature. The shear modulus was measured with a 1, 2, and 3 kilogram load at room temperature.

EXAMPLE IV

Example II was repeated except about 520 parts of a polybutene (Amoco Indopol H-300) was used and the gel rigidity found to be about substantially unchanged with respect to use of naphthenic oil alone.

EXAMPLE V

Example II was repeated except about 520 parts of a polypropene (Amoco C-60) was used and the gel rigidity found to be about substantially unchanged with respect to use of naphthenic oil alone.

EXAMPLE VI

Example II was repeated except about 520 parts of a polyterpene (Hercules Piccolyte S10) was used and the gel rigidity found to be about substantially unchanged with respect to use of naphthenic oil alone.

EXAMPLE VII

Example II was repeated except about 360 parts of a combined mixture of: 72 parts of a paraffinic oil (ARCO prime 200), 72 pars of a naphthenic oil (ARCO Tufflo 6014), 72 parts of a polybutene oligomer (Amoco Indopol H-200), 72 parts of a polypropene oligomer (Amoco Polypropene C-60), and 72 parts of a polyterpene oligomer (Hercules Piccolyte S10) was used and the gel rigidity found to be about substantially unchanged with respect to the use of naphthenic oil alone.

EXAMPLE VIII

Example III was repeated except 933 parts oil with 147 parts by weight of a high viscosity poly(styrene-ethylene-butylene-styrene) triblock copolymer containing 47 parts of a naphthenic process oil (Shell Kraton G 4609) having a styrene to ethylene and butylene ratio of about 33:67 was used and the physical properties were found to be about substantially unchanged with respect to the components used in Example III.

EXAMPLE IX

Example III was repeated except 933 parts oil with 147 parts by weight of a high viscosity poly(styrene-ethylene-butylene-styrene) triblock copolymer containing 47 parts of a paraffinic white petroleum oil (Shell Kraton G 4609) having a styrene to ethylene and butylene ratio of about 33:67 was used and the physical properties were found to be about substantially unchanged with respect to the components used in Example I.

EXAMPLE X

Example II was repeated except about 400 parts of oil was used and the properties measured were: tear propagation about $1.4\times10^6$ dyne/cm$^2$, growth in 180° bend under 50 gram load for 5,000 hours at room temperature, tensile strength about $4\times10^6$ dyne/cm2, elongation at break about 1,700%, tensile set about 0% at 1,200% elongation, compression set about 0% when tested under 5,000 gram load for 24 hours, and 100% snap back recovery after extension to 1,200%.

Examples XI-XIV-j below illustrate other modes of practice contemplated.

EXAMPLE XI

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 32:68 and the gel rigidity is found to be within the range of about 20 to about 800 gram Bloom.

EXAMPLE XII

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 34:66 and the gel rigidity is found to be within the range of about 20 to about 800 gram Bloom.

EXAMPLE XIII

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 36:64 and the gel rigidity is found to be within the range of about 20 to about 800 gram Bloom.

EXAMPLE XIV

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 38:62 and the gel rigidity is found to be within the range of about 20 to about 800 gram Bloom.

EXAMPLE XIV-a

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 31:69 and the gel rigidity is found to be within the range of about 10 to about 800 gram Bloom.

EXAMPLE XIV-b

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 37:63 and the gel rigidity is found to be within the range of about 10 to about 800 gram Bloom.

EXAMPLE XIV-c

The procedure of Example II is repeated and a poly (styrene-ethylene-butylene-styrene) (characterized by a Brookfield Viscosity of a 20 weight percent solids solution in toluene at 25° C. of at least about 1,800 cps.) is used having a styrene end block to ethylene and butylene center block ratio of about 19:81 and the gel rigidity is found to be within the range of about 10 to about 800 gram Bloom.

EXAMPLE XIV-d

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 20:80 and the gel rigidity is found to be within the range of about 10 to about 800 gram Bloom.

EXAMPLE XIV-e

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 38:62 and the gel rigidity is found to be within the range of about 10 to about 800 gram Bloom.

EXAMPLE XIV-f

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 29:71 and the gel rigidity is found to be within the range of about 10 to about 800 gram Bloom.

EXAMPLE XIV-g

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 26:74 and the gel rigidity is found to be within the range of about 10 to about 800 gram Bloom.

EXAMPLE XIV-h

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 22:78 and the gel rigidity is found to be within the range of about 10 to about 800 gram Bloom.

EXAMPLE XIV-i

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 25:75 and the gel rigidity is found to be within the range of about 10 to about 800 gram Bloom.

EXAMPLE XIV-j

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 26:74 and the gel rigidity is found to be within the range of about 10 to about 800 gram Bloom.

EXAMPLE XV

Example II is repeated except about 980 parts oil containing 100 parts of a $Fe_3O_4$ magnetic particle is used and the gel rigidity is found to be within the range of about 20 to 800 gram Bloom.

EXAMPLE XVI

The composition of EXAMPLE II is formed into wheels for a motorized and a free rolling vehicle capable of ascending or descending on a substantially glass, metal, and gloss painted inclined surface (greater than about 45 degree angle). It is contemplated that the non-adhesive tack nature of the composition may be useful as wheels or traction material for a vehicle capable of roving on the internal or external surfaces of a space ship or a space station under zero gravity conditions.

EXAMPLE XVII

Example II is repeated except the molten composition is casted onto a polyether, a polyester, a surlyn ionomer open cell sponge thereby displacing the air space within the sponge and the gel rigidity is found to be greater than about the sum of the combined rigidity of the composition and sponge alone.

EXAMPLE XVIII

The composition of Example II is casted unto the surface of a Duocel open cell metal sponge.

EXAMPLE XIX

The composition of Example II is casted unto a SCOTFOAM® ⅛" thick: 5, 10, 15, 20, 25, 30, 35, 40, 45, 50, 60, 70, 80, 90, 100, and 200 ppi foam sheet.

EXAMPLE XIX

The composition of Example II is casted unto shaped SCOTFOAM® articles (in the shapes of a crutch cushion, a cervical pillow, a bed wedge pillow, a leg rest cushion, a neck cushion, a bed pad, a elbow pad, a dermal pad, a wheelchair cushion, a helmet liner, a hot or cold a compress a pad, a exercise weight belt, a swab, a traction pad, a splint, a sling, a rib support, an orthopedic shoe sole, a brice cushions for the hand, wrist, finger, forearm, knee, leg, clavicle, shoulder, foot, ankle, neck, and back) having pore sizes (5, 10, 15, 20, 25, 30, 35, 40, 45, 50, 60, 70, 80, 90, 100, and 200 ppi) and are selected to match the need of the individual user.

EXAMPLE XX

The procedure of Example II is repeated and a poly (styrene-ethylene-butylene-styrene) triblock copolymer (characterized by a Brookfield Viscosity of a 20 weight percent solids solution in toluene at 25° C. of at least about 1,800 cps.) is used having a styrene end block to ethylene and butylene center block ratio of about 27:73 and the gel rigidity is found to be within the range of about 10 to about 800 gram Bloom.

While certain features of this invention have been described in detail with respect to various embodiments thereof, it will, of course, be apparent that other modifications can be made within the spirit and scope of this invention, and it is not intended to limit the invention to the exact details shown above except insofar as they are defined in the following claims.

What I claim is:

1. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed of the combination GnMnGn, GnGnMnGn, GnGnGnMnGnGn, GnMn, MnGnMn, MnGnGn, GnGnMn, MnMnGn, MnGnGnMn, GnMnGnMn, MnGnGnGn, MnMnMnGn, MnGnMnMn, MnGnMnGn, GnMnGnGn, GnMnMnGn, GnGnMnMnGn, GnGnMnGnMnMn, GnMnGnMnMn, GnMnGnMnGn, GnMnMnGnGn, GnGnGnMnMn, MnGnGnMnGn, MnGnMnGnMn, GnGnMnMnMn, GnMnMnGnMn, MnGnMnGnMnGn, GnGnMnGnMnGnMn, GnGnMnMnMnGn, GnGnMnGnMnMnGn,
GnMnGnMnGnMn,   GnMnGnMnGnGnMn,
MnGnGnMnGnMn,   GnGnMnMnGnGn,
MnMnGnGnMnMn,   MnGnGnMnGnGn,
GnGnMnGnGnMn, GnMnGnMnGn, MnMnMnGnMnM-nMn MnGnMnGnGnMn, GnMnGnMnGnMnGn,
MnGnMnGnMnMnGn, GnMnMnGnMnMnGn,
MnGnGnMnGnGnMn, GnMnGnMnGnMnGnMn,
GnGnMnMnGnGnMnMn, GnGnMnGnGnMnGnGn,
GnMnGnGnMnGnGnMnGn, GnGnMnGnMnGnMnGnGn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer is a linear, multi-arm, branched, or star shaped copolymer of the general configuration poly(styrene-ethylene-butylene-styrene), poly (styrene-ethylene-propylene-styrene), or a mixture thereof and optionally in combination with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene), low viscosity poly(styrene-ethylene-propylene-styrene), low viscosity poly(styrene-ethylene-butylene-styrene), poly(styrene-ethylene-butylene), polystyrene, polybutylene, poly (ethylene-propylene), poly(ethylene-butylene), polypropylene, or polyethylene, wherein said selected copolymer is a linear, branched, multiarm, or star shaped copolymer.

2. A composite article of claim 1, wherein said article is a vibration damper, a vibration isolator, a wrapper, a hand exerciser, a dental floss, a crutch cushion, a cervical pillow, a bed wedge pillow, a leg rest cushion, a neck cushion, a mattress, a bed pad, an elbow pad, a dermal pad, a wheelchair cushion, a helmet liner, a hot or cold compress pad, an exercise weight belt, or a traction pad.

3. A composite article of claim 1, wherein said article is a splint, sling, or brice cushion for the hand, wrist, finger, forearm, knee, leg, clavicle, shoulder, foot, ankle, neck, back, and rib or an orthopedic shoe sole.

4. A composite article formed from the composition of clam 1, wherein said triblock copolymer is characterized by a Brookfield Viscosity of a 20 weight percent solids solution in toluene at 25° C. of substantially greater than 1,800 cps.

5. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed of the combination GnGnMn, GnGnGnMnGn, GnMn, GnMnGn, MnGnMn, MnMnGn, MnGnGnMn, GnMnGnMn, MnGnGnGn, MnMnMnGn, MnMnGnGnMnMnMn, MnGnMnMn, MnGnMnGn, GnMnGnGn, GnMnMnGn, GnGnMnMn, GnGnMnGnMn, GnMnGnMnMn, GnMnGnMnGn, GnMnMnGnGn, GnGnGnMnMn, MnGnGnMnGn, MnGnMnGnMn, GnGnMnMnMn, GnMnMnGnMn, MnGnMnGnMnGn, GnGnMnGnMnGnMn, GnGnMnGnMnGnMn,
GnMnGnMnGnMn,   GnMnGnMnGnGnMn,
MnGnGnMnGnMn,   GnGnMnMnGnGn, MnMnGnGnMnMn, MnGnGnMnGnMn, MnGnGnMnGnGn, GnGnMnGnGnMn, MnGnMnGnGnMn, GnMnGnMnGnMnGn, MnGnMnGnMnMnGn, GnMnMnGnMnMnGn, MnGnGnMnGnGnMn, GnMnGnMnGnMnGnMn, GnGnMnMnGnGnMnMn, GnGnMnGnGnMnGnGn, GnMnGnGnMnGnGnMnGn, GnGnMnGnMnGnMnGnGn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented gel, a non-oriented gel, a tacky gel or a non-tacky gel; said triblock copolymer is a linear, multi-arm, branched, or star shaped copolymer of the general configuration poly(styrene-ethylene-propylene-styrene) in combination with a selected amount of poly(styrene-ethylene-propylene) or poly(styrene-ethylene-butylene), wherein said selected copolymer is a linear, branched, multiarm, or star shaped copolymer.

7. A composite article comprising of a thermoplastic, heat formable and heat reversible gelatinous elastomer composition, G, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, GnGnMn, GnGnGnMn, GnGnGnGnMn, GnGnGnGnGnMn, GnMnGn, GnMnmnGn, GnMnmnMnGn, MnGnMn, MnGnMnGnMn, MnMnGnMnMn, MnMnMnGnMnMnMn, MnMnMnGnMnGnMnGnMnMnMn, MnMnMnGnMnMnGnMnMnMn, MnMnMnGnMnMnMnGnMnMnMn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer is a linear, multi-arm, branched, or star shaped copolymer of the general configuration poly(styrene-ethylene-butylene-styrene), poly(styrene-ethylene-propylene-styrene), or a mixture thereof and optionally in combination with a selected amount of at least one polymer or copolymer selected from the group consisting of poly(styrene-ethylene-propylene), poly(styrene-ethylene-butylene), polystyrene, polybutylene, poly(ethylene-propylene), poly(ethylene-butylene), polypropylene, or polyethylene, wherein said selected copolymer is a linear, branched, multiarm, or star shaped copolymer.

8. A composite article comprising of a thermoplastic, heat formable and heat reversible gelatinous elastomer composition, G, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, GnMnGn, GnMnGnMnGn, GnMnGnMnGnMnGn, GnMnGnMnGnMnGnMnGn, MnGnMn, MnMnGnMnMn, MnMnMnGnMnmnmn or any permutations of said combination, wherein when n is a subscript of M, n is the same or different selected from the group consisting of foam, plastic, fabric, metal, concrete, wood, glass, ceramics, synthetic resin, synthetic fiber or refractory materials; wherein when n is a subscript of G, n denotes the same or a different rigidity gel, an oriented (optically birefringent) gel, a non-oriented gel, a tacky gel or a non-tacky gel; said triblock copolymer is a linear, multi-arm, branched, or star shaped copolymer of the general configuration poly(styrene-ethylene-butylene-styrene), poly(styrene-ethylene-propylene-styrene), or a mixture thereof and optionally in combination with a selected amount of at least one polymer or copolymer selected from the group consisting of poly(styrene-ethylene-propylene), poly(styrene-ethylene-butylene), polystyrene, polybutylene, poly(ethylene-propylene), poly(ethylene-butylene), polypropylene, or polyethylene, wherein said selected copolymer is a linear, branched, multiarm, or star shaped copolymer.

* * * * *

REEXAMINATION CERTIFICATE (4166th)
United States Patent [19]
Chen

[11] B1 5,633,286
[45] Certificate Issued Oct. 10, 2000

[54] GELATINOUS ELASTOMER ARTICLES

[75] Inventor: John Y. Chen, Pacifica, Calif.

[73] Assignee: Applied Elastomerics, Inc., Pacifica, Calif.

Reexamination Request:
No. 90/004,796, Oct. 9, 1997

Reexamination Certificate for:
Patent No.: 5,633,286
Issued: May 27, 1997
Appl. No.: 08/288,690
Filed: Aug. 11, 1994

Related U.S. Application Data

[63] Continuation-in-part of application No. PCT/US94/07314, Jun. 27, 1994, which is a continuation-in-part of application No. PCT/US94/04278, Apr. 19, 1994, which is a continuation-in-part of application No. 07/957,290, Oct. 6, 1992, Pat. No. 5,334,646, and a continuation-in-part of application No. 08/152,734, Nov. 15, 1993, Pat. No. 5,624,294, and a continuation-in-part of application No. 08/152,735, Nov. 15, 1993, Pat. No. 5,508,334, and a continuation-in-part of application No. 08/114,688, Aug. 30, 1993, Pat. No. 5,475,890, which is a continuation-in-part of application No. 07/934,027, Aug. 24, 1992, Pat. No. 5,239,723, and a continuation-in-part of application No. 07/935,540, Aug. 24, 1992, Pat. No. 5,336,708, which is a continuation-in-part of application No. 07/705,711, May 23, 1991, Pat. No. 5,262,468, and a continuation-in-part of application No. 07/876,118, Apr. 29, 1992, Pat. No. 5,324,222, and a continuation-in-part of application No. 07/705,096, May 23, 1991, said application No. 07/876,118, and application No. 07/705,096, each is a continuation of application No. 07/527,058, May 21, 1990, abandoned, said application No. 07/705,711, and application No. 07/527,058, each is a continuation of application No. 07/211,426, Jun. 24, 1998, Pat. No. 5,153,254, which is a continuation-in-part of application No. 06/921,752, Oct. 21, 1986, abandoned, which is a continuation-in-part of application No. 06/572,172, Jan. 18, 1984, Pat. No. 4,618,213, which is a continuation-in-part of application No. 06/458,703, Jan. 17, 1983, abandoned, which is a continuation-in-part of application No. 06/134,977, Mar. 28, 1980, Pat. No. 4,369,284, which is a continuation-in-part of application No. 05/916,731, Jun. 19, 1978, abandoned, which is a continuation-in-part of application No. 05/815,315, Jul. 13, 1977, abandoned, which is a continuation-in-part of application No. 05/778,343, Mar. 17, 1977, abandoned.

[51] Int. Cl.[7] ............................... C08K 5/00; C08K 5/01; A42B 3/00; C08L 3/00
[52] U.S. Cl. ................................. 524/474; 2/411; 5/632; 5/636; 5/640; 132/321; 135/68; 135/71; 135/72; 135/82; 297/391; 297/392; 297/394; 297/397; 297/411.2; 297/423.1; 524/476; 524/470; 524/505; 427/162; 428/52; 521/148; 525/95
[58] Field of Search ................................... 524/474, 476, 524/490, 505; 525/95; 2/411; 5/632, 636, 640; 132/321; 135/68, 71, 72, 82; 297/391, 392, 394, 397, 411.2, 423.1, DIG. 1, DIG. 4; 427/162; 428/52; 521/148

[56] References Cited

U.S. PATENT DOCUMENTS

| | | | |
|---|---|---|---|
| Re. 27,145 | 6/1971 | Jones | 260/880 |
| 2,993,874 | 7/1961 | Hoel | 260/27 |
| 3,149,182 | 9/1964 | Porter | 260/879 |
| 3,239,476 | 3/1966 | Harlan | 260/27 |
| 3,239,478 | 3/1966 | Harlan | 260/27 |

(List continued on next page.)

FOREIGN PATENT DOCUMENTS

| | | |
|---|---|---|
| 146163 | 11/1984 | European Pat. Off. |
| 285181 | 4/1988 | European Pat. Off. |
| 362850 | 4/1990 | European Pat. Off. |
| 439180 | 1/1991 | European Pat. Off. |
| 483370 | 4/1991 | European Pat. Off. |
| 2019416 | 4/1979 | United Kingdom . |
| WO8800603 | 7/1987 | WIPO . |
| WO9005166 | 9/1989 | WIPO . |

OTHER PUBLICATIONS

Allen, et al, Comprehensive Polymer Science–vol. 7; 1994; pp. 416–431.

Kirk–Othmer; Encyclopedia of Chemical Technology; 1994; 4$^{th}$ Edition; pp. 17–37.

Garder, William; Gardner's Chemical Synonyms and Trade Names; 1994.

Holden et al; Thermoplastic Elastomers; 2$^{nd}$ Edition; 1996; Chapter 1–pp. 1–26; Chapter 3–pp. 27–70; Chapter 4–pp. 71–100.

Kuraray MSDS Septon 2006, Apr. 25, 1991.

Kuraray MSDS Septon 4055, Apr. 25, 1991.

Kuraray "SEP/SEPS" Typical Properties of SEP/EPS (4055), Apr. 25, 1991.

(List continued on next page.)

*Primary Examiner*—Herbert J. Lilling

[57] ABSTRACT

Novel composites are formed from a low rigidity oriented and non-oriented gelatinous elastomer composition of poly(styrene-ethylene-butylene-styrene) or poly(styrene-ethylene-[proplene]*propylene*-styrene) triblock copolymer and high levels of a plasticizing oil. The gelatinous elastomer composition is physically interlocked with an open cell sponge thereby displacing the air space within the sponge and the gel rigidity is found to be greater than about the sum of the combined rigidity of the gelatinous elastomer composition and sponge alone. The gelatinous elastomer composite exhibits a novel combination of properties including unexpectedly high elongation and tensile strength and excellent shape retention after extreme deformation under high-velocity impact and stress conditions. The gelatinous elastomer composites can be made firm or soft and flexible. These and other properties are particularly essential for the gelatinous elastomer composites to have utility as toys, therapeutic hand exercising grips, shock absorbers, acoustical isolators, vibration dampers, vibration isolators, wrappers, hand exercisers, crutch cushions, cervical pillows, bed wedge pillows, leg rest cushions, neck cushions, bed pads, elbow pads, dermal pads, wheelchair cushions, helmet liners, hot or cold compress pads, exercise weight belts, swabs, traction pads, splints, slings, rib supports, orthopedic shoe soles, [brice] *brace* cushions for the hand, wrist, finger, forearm, knee, leg, clavicle, shoulder, foot, ankle, neck, back, and the like.

U.S. PATENT DOCUMENTS

| | | | |
|---|---|---|---|
| 3,265,765 | 8/1966 | Holden | 260/876 |
| 3,325,430 | 6/1967 | Grasley | 260/25 |
| 3,333,024 | 7/1967 | Haefele | 260/880 |
| 3,464,850 | 9/1969 | Haefele | 117/135.5 |
| 3,485,787 | 12/1969 | Haefele | 260/33.6 |
| 3,595,942 | 7/1971 | Wald | 260/880 |
| 3,614,836 | 10/1971 | Snyder | 36/2.5 |
| 3,660,849 | 5/1972 | Jonnes | 2/2.1 |
| 3,676,387 | 7/1972 | Lindlof | 260/28.5 |
| 3,756,977 | 9/1973 | Yoshimoto | 260/33.6 |
| 3,792,005 | 2/1974 | Harlan | 260/22 |
| 3,810,957 | 5/1974 | Lunk | 260/876 |
| 3,821,149 | 6/1974 | Makowski | 260/30.6 |
| 3,827,999 | 8/1974 | Crossland | 260/33.6 |
| 3,830,767 | 8/1974 | Condon | 260/28.5 |
| 3,898,208 | 8/1975 | Krause | 260/85.1 |
| 3,929,715 | 12/1975 | Noweil | 260/34.2 |
| 3,933,723 | 1/1976 | Grenness | 260/33.6 |
| 3,965,019 | 6/1976 | St. Clair | 252/59 |
| 4,006,116 | 2/1977 | Dominguez | 260/33.6 |
| 4,032,459 | 6/1977 | Crossland | 252/51.5 |
| 4,036,910 | 7/1977 | Anderson | 525/338 |
| 4,039,629 | 8/1977 | Himes | 260/880 |
| 4,041,103 | 8/1977 | Davison | 260/857 |
| 4,080,348 | 3/1978 | Korpman | 260/27 |
| 4,136,071 | 1/1979 | Korpman | 260/27 |
| 4,313,867 | 2/1982 | Duvdevani | 260/33.6 |
| 4,369,284 | 1/1983 | Chen | 524/276 |
| 4,432,607 | 2/1984 | Levy . | |
| 4,481,323 | 11/1984 | Sterling | 524/269 |
| 4,511,354 | 4/1985 | Sterling | 604/98 |
| 4,618,213 | 10/1986 | Chen | 524/476 |
| 4,709,982 | 12/1987 | Corne . | |
| 4,716,183 | 12/1987 | Gamarra . | |
| 4,968,747 | 11/1990 | Mallikarjun | 525/74 |
| 5,093,422 | 3/1992 | Himes | 525/98 |
| 5,098,421 | 3/1992 | Zook . | |
| 5,112,900 | 5/1992 | Buddenhagen | 524/484 |
| 5,126,182 | 6/1992 | Douglas | 428/90 |
| 5,153,254 | 10/1992 | Chen | 524/505 |
| 5,159,022 | 10/1992 | Ikematu | 525/250 |
| 5,210,147 | 5/1993 | Southwick | 525/314 |
| 5,313,019 | 5/1994 | Brusselmans et al. | 174/93 |
| 5,442,004 | 8/1995 | Sutherland | 524/140 |
| 5,459,193 | 10/1995 | Anderson . | |
| 5,475,890 | 12/1995 | Chen . | |
| 5,508,334 | 4/1996 | Chen . | |
| 5,541,250 | 7/1996 | Hudson | 524/505 |
| 5,559,165 | 9/1996 | Paul . | |
| 5,580,572 | 12/1996 | Mikler | 424/448 |
| 5,618,882 | 4/1997 | Hammond . | |
| 5,655,947 | 8/1997 | Chen . | |

OTHER PUBLICATIONS

Winding et al "Polymeric Materials" pp. 119–122 "Injection Molding" 1961 Publisher McGraw Hill Book Company.

Shell Chemical Company Kraton thermoplastic rubber typical properties data sheet (Apr. 1980).

BeOK Thermo–Gel (patented polymer gel) products.

Knit–Rite, Inc. Product sheet: impregnated sheaths, soft socket gel–liner and silosheath, gel–liner and gel suspension sleeve, and elbow & wrist supports.

Silipos advanced polymer technology product catagoue.

Silipos manual (1994) for US and Worldwide distribution.

Shell Technical Bulletin SC:1102–1989.

Shell Kraton SC:198–80 Jul. 1980 SM, pp. 2–3.

Figure 2A:
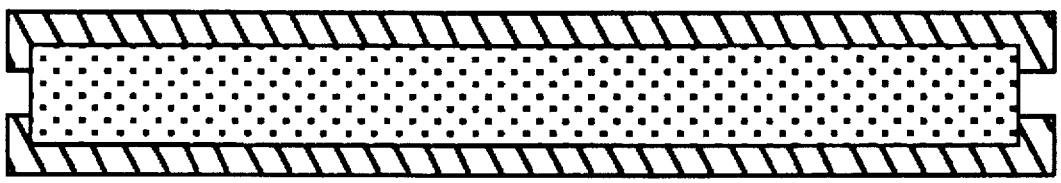
Figure 2B:
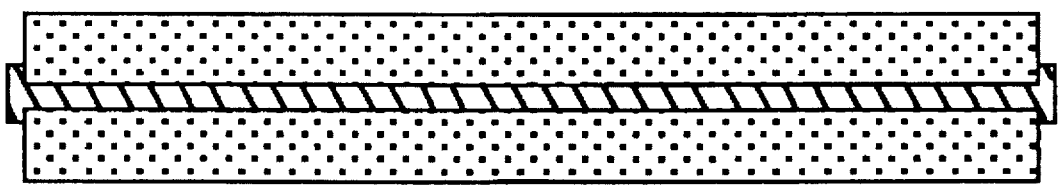
Figure 2C:
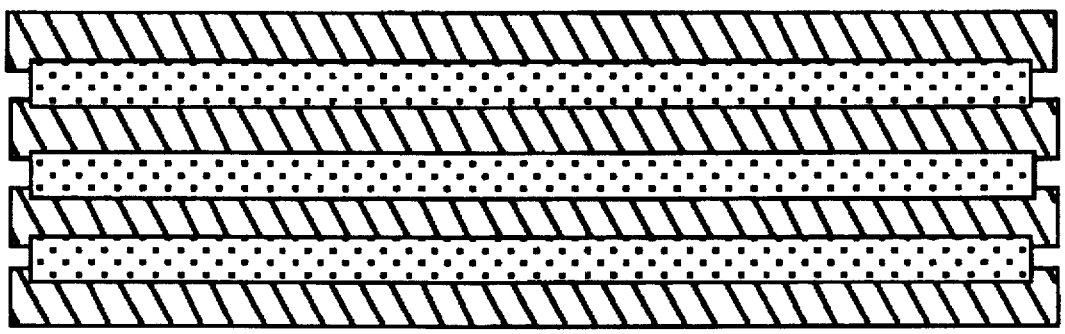
Figure 2D:
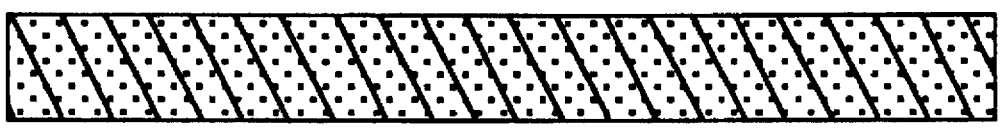
Figure 3:
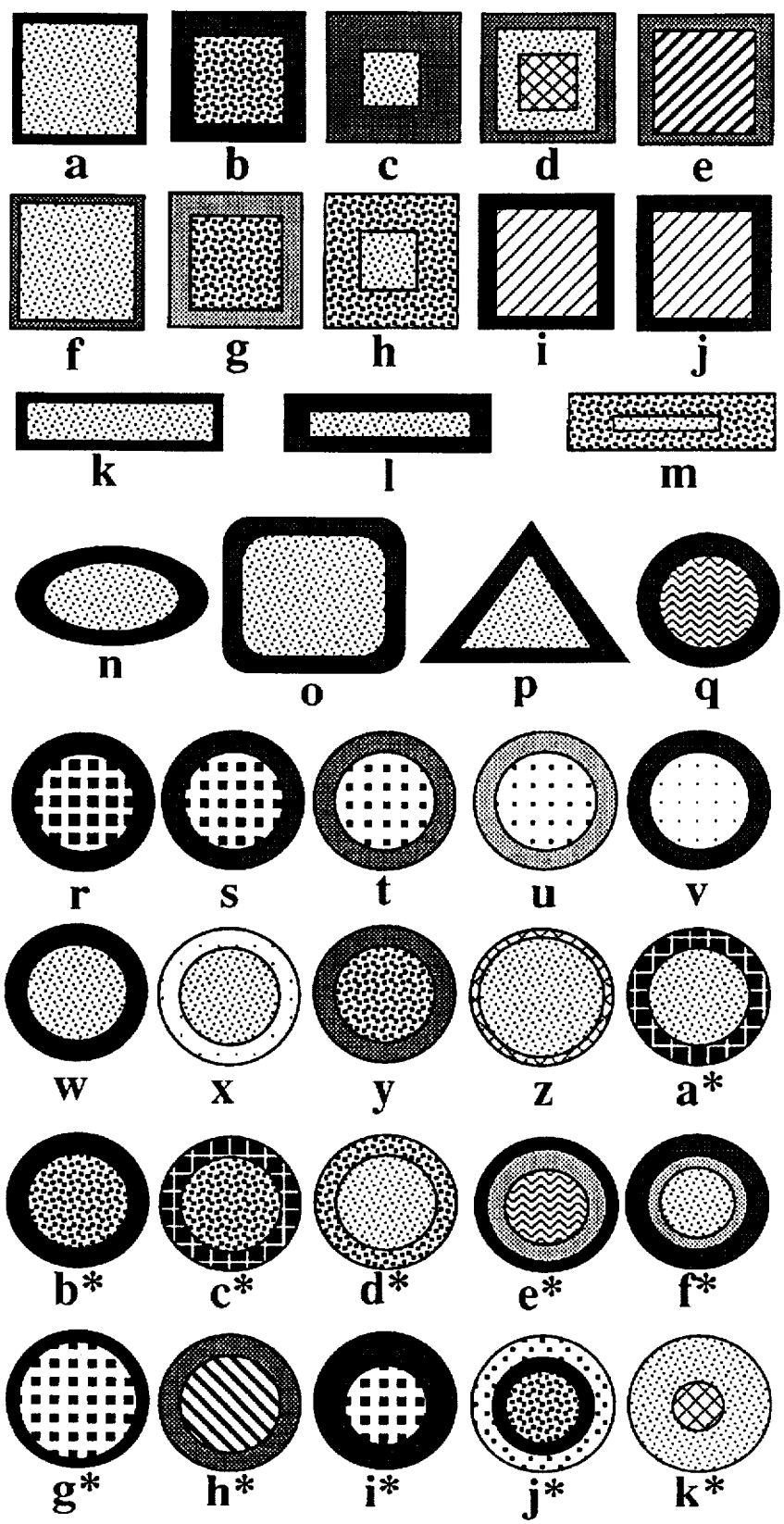
FIGS. 3a–3d. Representative sectional view of composite articles.
Figure 3A:
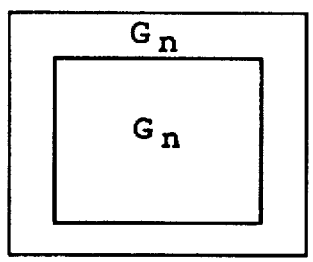
Figure 3B:
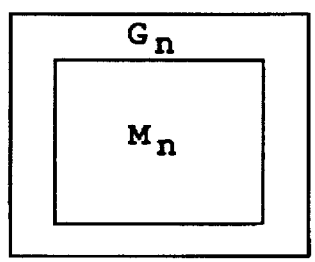
Figure 3C:
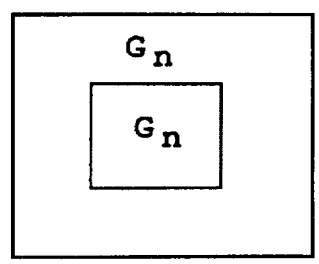
Figure 3D:
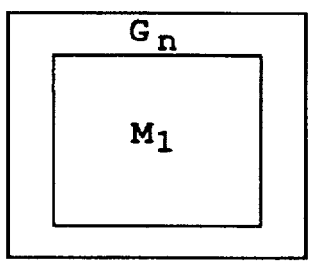
Figure 3E:
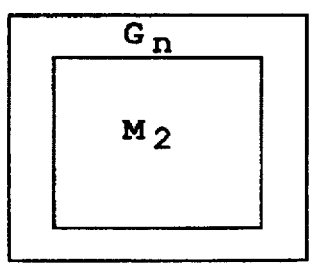
Figure 3F:
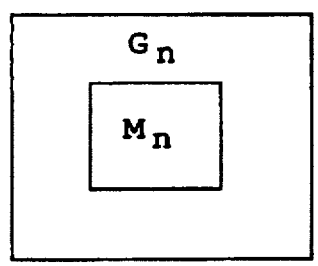
Figure 3G:
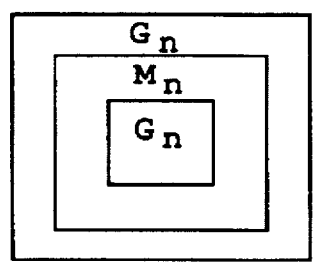
Figure 3H:
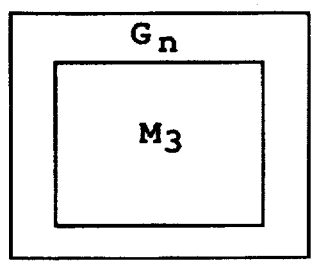
Figure 3I:
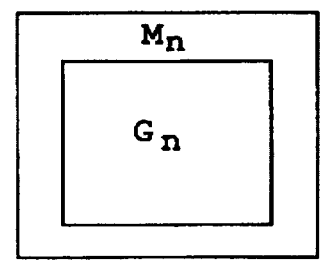
Figure 3J:
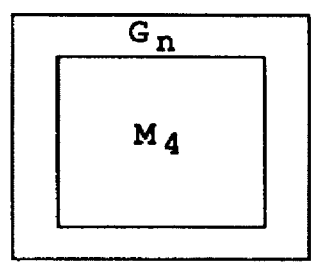
Figure 3K:
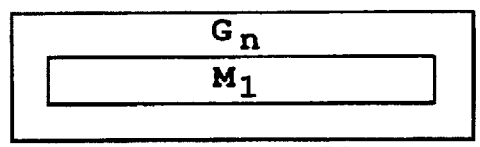
Figure 3M:
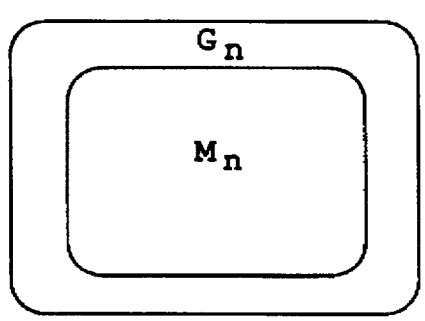
Figure 3L:
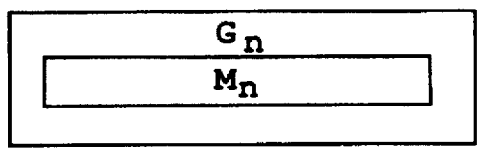
Figure 3N:
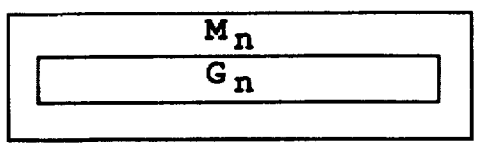
Figure 4A:
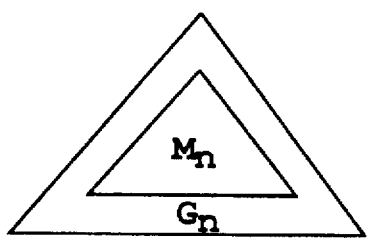
FIGS. 4a–4w. Representative sectional view of composite articles.
Figure 4B:
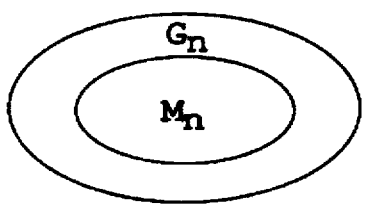
Figure 4C:
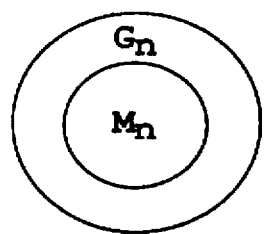
Figure 4D:
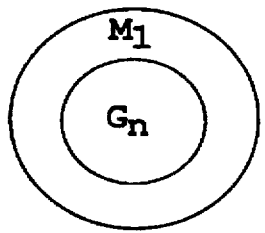
Figure 4E:
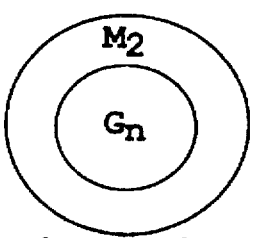
Figure 4F:
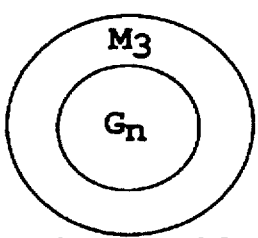
Figure 4G:
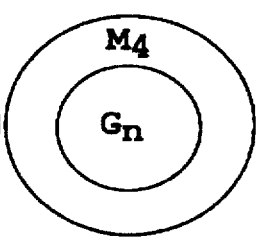
Figure 4H:
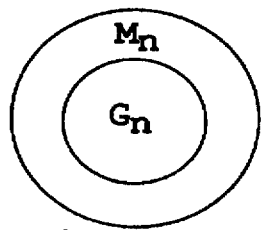
Figure 4I:
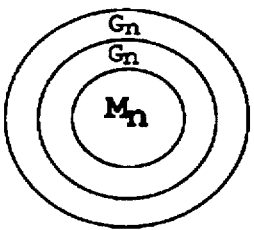
Figure 4J:
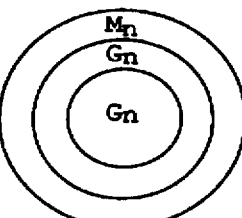
Figure 4K:
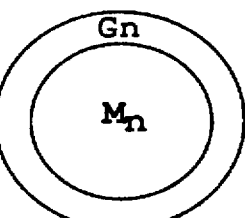
Figure 4L:
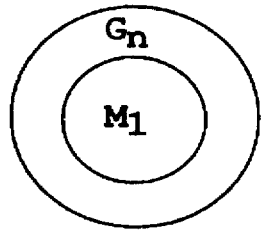
Figure 4M:
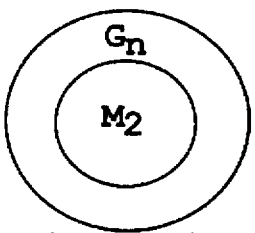
Figure 4N:
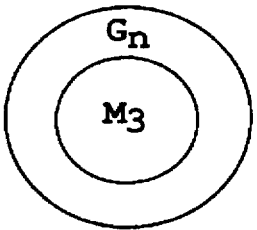
Figure 4O:
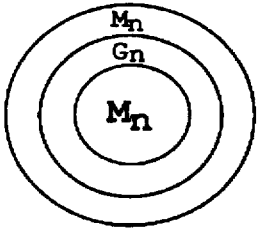
Figure 4P:
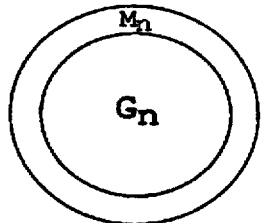
Figure 4Q:
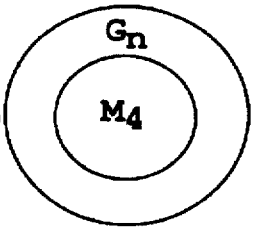
Figure 4R:
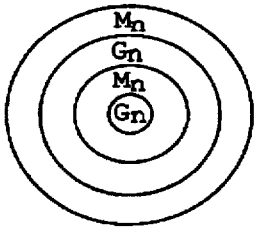
Figure 4S:
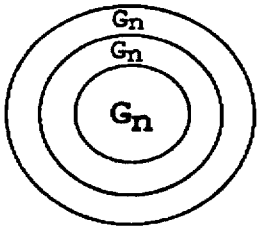
Figure 4T:
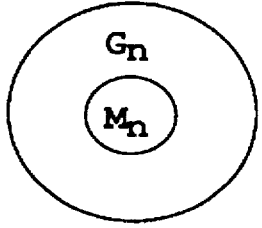
Figure 4U:
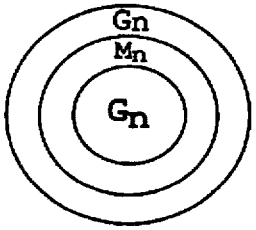
Figure 4V:
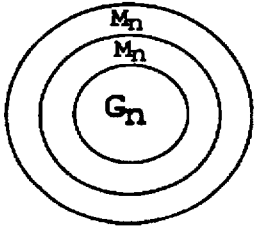
Figure 4W:
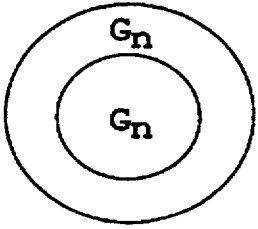

Shell Technical Bulletin SC:65–75 Oct. 1975 FIG 1–2 p. 3, FIG. 14 p. 12.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 63–67 through column 2, lines 1–51:

The embodiments of the composite articles of the invention comprises a thermoplastic, heat formable and heat reversible gelatinous elastomer composition, G, which is physically interlocked with a selected material Mn, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed from the combination GnMn, GnMnGn, MnGnMn, MnGnGn, [GnGnMn, MnGnMn,] MnMnGn, MnGnGnMn, [GnMnGnMn, MnGnGnG,] MnMnMnGn, MnGnMnMn, MnMnGnMnMn, MnGnMnGn, GnMnGnGn, GnMnGnGn, GnGnMnMn, GnGnMnGnMn, GnGnMnGn, GnGnGnMnGnGn, GnMnGnMnMn, GnMnGnMnGn, [GnMnMnGnGn,] GnGnGnMn, GnGnGnMnGn, GnGnGnGnMn, GnGnGnMnMn, GnGnGnGnGnMn, MnGnGnMnGn, MnGnMnGnMn, [GnGnMnmnM,] *GnGnMnMnM,* GnMnMnGnMn, MnGnMnGnMnGn, GnGnMnMnGn, GnGnMnGnMnGn, [GnMnGnMnGnMn,] GnMnMnGnGnMn, MnGnGnMnGnMn, GnGnMnMnGnGn, MnMnGnGnMnMn, MnGnGnMnGnMn, MnGnGnMnGnMn, MnGnGnMnGnGn, GnGnMnGnGnMn, GnMnGnMnGnMn, MnMnMnGnMnMnM, MnGnMnGnGnMn, GnMnGnMnGnMnGn, MnGnMnGnMnMnGn, GnMnMnGnMnMnGn, MnGnGnMnGnGnMn, GnMnGnMnGnMnGnMn, GnGnMnMnGnMnMn, GnGnMnGnGnMnGnGn, [MnGnGnMnGnGnMn,] GnMnGnGnMnGnGnMnGn, GnGnMnGnMnGnMnGnGn, [MnMnGnGnMnGnGnMnGn] GnGnMnGnMnGnMnGnGn, GnMnMnMnGn, MnMnMnGnMnGnMnMnM, MnMnMnGnMnMnGnMnMnM, MnMnMnGnMnMnMnGnMnMnM, GnMnGnMnGnMnGnMnGn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, said triblock copolymer is a linear, multi-arm, branched, or star shaped copolymer of the general configuration poly(styrene-ethylene-butylene-styrene), poly(styrene-ethylene-propylene-styrene), or a mixture thereof and optionally in combination with a selected amount of at least one polymer or copolymer selected from the group consisting of poly(styrene-butadiene-styrene), poly(styrene-butadiene)*n,* poly(styrene-isoprene-styrene), poly(styrene-isoprene)*n,* poly(styrene-ethylene-propylene)*n,* low viscosity poly(styrene-ethylene-propylene-styrene), low viscosity poly(styrene-ethylene-butylene-styrene), poly(styrene-ethylene-butylene)*n,* polystyrene, polybutylene, poly(ethylene-propylene), poly(ethylene-butylene), [polyproply-ene] *polypropylene,* or polyethylene, wherein said selected copolymer is a linear, branched, multiarm, or star shaped copolymer *as conventionally denoted by n, a positive number.*

Column 3, lines 3–18:

Applicant's related parent application Ser. No. 921,752, filed Oct. 21, 1986, and application Ser. No. 211,426, filed Jun. 24, 1988 describe various useful gel articles and forming gel-foam or gel-sponge composite articles. The gelatinous elastomer composition of the present invention have various novel properties which makes them useful, for example, as hand grips sold under the trademark Recovery®. The hand grips can distribute the gripping force over the entire contact surface of the hand without high stree concentrations. The grips are ideal for exercises requiring extreme softness and adequate distribution of the gripping force approximating that of hydrostatic pressure. Hand grips having greater rigidities are sold under the trademark Stamina™ and Endurance™. These grips require an increase in [the] the triblock copolymer component of the overall gelatinous elastomer composition.

Column 3, lines 36–43:

A further embodiment of the invention is to provide oriented gels with improved high strength alignment properties as evidenced by optical techniques such as viewing oriented gel in plane-polarized light. Oriented gels exhibit birefringence in the relaxed unextended state. Oriented gels with improved strength are suitable for use as dental floss since they do not break as eas*i*ly as un-oriented gels of the same rigidity.

Column 3, lines 44–67 through column 4, lines 1–5:

Oriented gels [aliegned] *aligned* by controlled stretching during the gel's transition from a heated, non melting, non flowing state and the cooled solid gel state produces strong gels which are found to have greater tensile strength than gels of the same rigidity which have not been stretched to a selected degree during its heating and cooling histories. Gels which are selectively stretched during its (non melt flowing) heated state and rapidly coo[l]*l*ed by flowing air, cold liquid bath or in contact with a cool surface exhibit optical birefringence when viewed under plane-polarized light. The degree of [streaching] *stretching* during the gels cooling history from the heated state can vary. Stretching of at least about 50% to more than about 1000% are of advantage to produce [birefrigence] *birefringence* and stronger gels. [Birefrigence] *Birefringence* is not observed in relaxed gels which do not undergo stretching during its heating and cooling histories. Slight to very strong birefringence are observed in [rleaxed] *relaxed* gels which are stretched during its heating and cooling histories. it is evident that stressing the gel during its cooling history as it cools from the heated state produce unexpected stronger oriented gels. We therefore consider oriented gels to be a new and novel composition physically different from the less stronger gels formed without stressing during the gels cooling history. Oriented gels may be formed in combination with various substrates such as described below. In past situations where in order to [obatin] *obtain* stronger gel strength, gels with higher rigidities and lower plasticizer content must be used, it is now possible to make a oriented gel with the same plasticizer content having a higher useful gel strength.

Column 4, lines 14–22:

The lamination of varying rigidities to produce an article (e.g. crutch cushions, cervical pillows, bed wedge pillows, leg rest cushions, neck cushions, bed pads, elbow pads, dermal pads, wheelchair cushions, rib supports, orthopedic shoe soles, [brice] *brace* cushions, etc.) can be eliminated by Column 4, lines 37–44:

The gelatinous elastomer composite articles can be formed in combination with other materials, such as open cell foam and sponges, other polymeric or elastomeric (Kraton) materials, porous materials, [multi-layered] *multi-layered* coatings, signal layered, composite layered materials. The opened cell sponge when dipped into the instant composition with form an interpenetrating physical networks (interlocking of gel and foam (FIG. 2d).

Column 5, lines 11–29:

Triblock copolymer gels especially suitable for use in forming the gel components of the composites of the invention include: SEBS gels; examples include: (a) Kraton G 1651, G 1654X gels; (b) Kraton G 4600 gels; (c) Kraton G 4609 gels; other less suitable SEBS oil gels; examples include: (d) Tuftec H 1051 gels; (e) Tuftec H 1041 gels; (f) Tuftec H 1052 gels. Gels made from blends (polyblends) of (a)–(f) with other polymers and copolymers includes: SEBS-SBS gels; SEBS-SIS gels; SEBS-(SEP) gels; SEBS-(SB)n gels; SEBS-(SEB)n gels; SEBS-(SEP)n gels; SEBS-(SI)n gels; SEBS-(SI) multiarm gels; SEBS-branched copolymers gels; SEBS-star shaped copolymer gels; gels made from blends of (a)–(f) with other homopolymers include: SEBS/polystyrene gels; SEBS/polybutylene gels; SEBS/polyethylene gels; SEBS/polyprop[o]ylene gels. Other suitable thermoplastic elastomers in blends suitable for making gels include SEP/SEBS oil gels, SEP/SEPS oil gels, SEP/SEPS/SEB oil gels, SEPS/SEBS/SEP oil gels, SEB/SEBS, EB-EP/SEBS, SEBS/EB, SEBS/EP, SEPS/SEB, etc. *As a matter of convention, the letter n denotes a positive number.*

Column 5, lines 54–67 through column 6, lines 1–10:

The most preferred gels forming the composites of the invention comprise a high viscosity triblock copolymers which have the more general configuration A-B-A wherein each A is a crystalline polymer end block segment of polystyrene; and B is a elastomeric polymer center block segment of poly(ethylene-butylene). The poly(ethylene-butylene) and polystyrene portions are incompatible and form a two-phase system consisting of sub-micron domains of glassy polystyrene interconnected by flexible poly(ethylene-butylene) chains. These domains serve to crosslink and reinforce the structure. This physical elastomeric network structure is reversible, and heating the polymer above the softening point of polystyrene temporarily disrupt the structure, which can be restored by lowering the temperature. This also applies to high viscosity poly(styrene-ethylene-propylene-styrene) [triblick] *triblock* copolymers. Most recent reviews of triblock copolymers are found in the "Encyclopedia of Polymer Science and Engineering", vol. 2 and 5, 1987-1988; "Thermoplastic Elastomers", Modern Plastic Encyclopedia, 1989; and Walker, B. M., Ed,. et al., Handbook of Thermoplastic Elastomers, Van Nostrand Reinhold Co., 2nd Edition, 1988. There publications are incorporated herein by reference).

Column 7, lines 19–23:

Examples of moderate to high viscosity SEPS triblock and S-E-EPS-S block copolymers includes Kuraray's 2006 *and* 4055 which exhibits a solution viscosities at 10 weight %, 30° C[.] of about 7.1 and 59 (P) *Poise* respectively and styrene contents by weight of about 35% and 30% respectively.

Column 7, lines 43–58:

Other polymers and copolymers (in major or minor amounts) can be melt blended with the SEBS as mentioned above without substantially decreasing the desired properties. Such polymers may also be utilized in one or more regions of the airfoils of the invention; these include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, (SEPS) styrene-ethylene-propylene-styrene block copolymers, (SB)n styrene-butadiend and (SEB)n, (SEBS)n, (SEP)n, (SI)n styrene-isoprene multi-arm, branched, and star shaped copolymers and the like, *wherein the subscript n conventionally denotes a positive number.* Still, other homopolymers can be utilized in minor amounts; these include: polystyrene, polybutylene, polyethylene, polyprop[o]ylene and the like.

Column 8, lines 23–49:

Additives useful in the gel of the present invention include: tetrakis[methylene 3,-(3'5'-di-tertbutyl-4"-hydroxyphenyl) propionate] methane, octadecyl 3-(3",5"-di-tert-butyl-4"-hydroxyphenyl) propionate, distearyl-pentaerythritol-diproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl] benzene),4,4"-methylenebis(2,6-di-tert-butylphenol), [steraric] *stearic* acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, calcium sterate, other metal sterates, waxes (e.g. polyethylene, polypropylene, microcrystalline, carnauba, paraffin, montan, candelilla, beeswax, ozokerite, ceresine, and the like). The gel can also contain metallic pigments (aluminum and brass flakes), TiO2, mica, fluorescent dyes and pigments, phosphorescent pigments, aluminatrihydrate, antimony oxide, iron oxides (Fe3O4, -Fe2O3, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on Magnetic Materials, Publication NMAB-426, National Academy Press (1985) is incorporated herein by reference.

Column 8, lines 56–67 through column 9, lines 1–6:

An advantage of making non-sticking, non-tacky gels is the use of waxes, [steraric] *stearic* acid and waxes, metal sterate and waxes, metal sterate and [steraric] *stearic* acid. The use of [steraric] *stearic* acid alone do not reduce tack. The amount of [steraric] *stearic* acid is also important. The ratio of 200 grams [steraric] *stearic* acid to 2,000 gram of SEBS (a ratio of 0.1) will result in spotted tack reduction on the surface of the gel. A ratio of 250 to 2,000 will result in spotted [crystalized] *crystallized* regions on the surface of the gel or spotted tack reduction. A ratio of 300 to 2,000 will result in complete tack reduction with large crystallized regions on the surface of the gel. When microcrystalline waxes are incorporated together with [steraric] *stearic* acid, the [crystalization] *crystallization* of [steraric] *stearic* acid completely [disapears] *disappears* from the surface of the gel. For example excellent result is achieved with 200 grams of [steraric] *stearic* acid, 150 grams of microcrystalline wax and 2,000 grams of SEBS. The same excellent is achieved when SEBS is adjusted to 3,000 grams, 4,000 grams, etc. The same result is achieved with SEPS.

Column 10, lines 32–44:

The gelatinous elastomer articles moulded from the instant compositions have various additional important advantages in that they do not crack, creep, tear, crack, or rupture in [flextural] *flexural*, tension, compression, or other deforming conditions of normal use; but rather the moulded articles made from the instant composition possess the intrinsic properties of elastic memory enabling the articles to recover and retain its original moulded shape after many extreme deformation cycles as compared to prior art triblock copolymer oil-extended compositions. In applications where low rigidity, high elongation, good compression set and excellent tensile strength are important, the instant compositions would be preferred.

Column 16, lines 49–61:

EXAMPLE XIX

The composition of Example II is casted unto shaped Scotfoam® articles (in the shapes of a cruch cushion, a cervical pillow, a bed wedge pillow, a leg rest cushion, a neck cushion, a bed pad, a elbow pad, a dermal pad, a wheelchair cushion, a helmet liner, a hot or cold a compress a pad, a exercise weight belt, a swab, a traction pad, a splint, a sling, a rib support, an orthopedic shoe sole, a [brice] *brace* cushions for the hand, wrist, finger, forearm, knee, leg, clavicle, shoulder, foot, ankle, neck, and back) having pore sizes (5, 10, 15, 20, 25, 30, 35, 40, 45, 50, 60, 70, 80, 90, 100, and 200 ppi) and are selected to match the need of the individual user.

AS A RESULT OF REEXAMINATION, IT HAS BEEN DETERMINED THAT:

Claims 1–8 are determined to be patentable as amended.

New claims 9–27 are added and determined to be patentable.

1. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel regidity of from about 20 to about 800 gram Bloom; said composite formed of the combination GnMnGn, GnGnMnGn, GnGnGnMnGnGn, [GnMn,] MnGnMn, MnGnGn, [GnGnMn,] MnMnGn, MnGnGnMn, GnMnGnMn, MnGnGnGn, MnMnMnGn, MnGnMnMn, MnGnMnGn, GnMnGnGn, GnMnMnGn, GnGnMnMn, GnGnMnGnMn, GnMnGnMnMn, GnMnGnMnGn, GnMnMnGnGn, GnGnGnMnMn, MnGnGnMnGn, MnGnMnGnMn, GnGnMnMnMn, GnMnMnGnMn, MnGnMnGnMnGn, GnGnMnMnGn, GnGnMnGnMnGn, GnMnGnMnGnMn, GnMnMnGnGnMn, MnGnGnMnGnMn, GnGnMnMnGnGn, MnMnGnGnMnMn, *MnGnGnMnGnMn,* MnGnGnMnGnGn, GnGnMnGnGnMn, [GnMnGnMnGn,] MnMnMnGnMnMnMn, MnGnMnGnGnMn, GnMnGnMnGnMnGn, GnMnGnMnMnMnGn, GnMnMnGnMnMnGn, [MnGnGnMnGnGnMn,] GnMnGnMnGnMnGnMn, GnGnMnGnGnMnGnMnMn, GnGnMnGnGnMnGnGn, *MnGnGnMnGnGnMn,* GnMnGnGnMnGnGnMnGn, GnGnMnGnMnGnMnGnGn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer is a linear, multi-arm, branched, or star shaped copolymer of the general configuration poly(styrene-ethylene-butylene-styrene), poly (styrene-ethylene-propylene-styrene), or a mixture thereof; and optionally in combination with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)*n,* low viscosity poly(styrene-ethylene-propylene-styrene), low viscosity poly(styrene-ethylene-butylene-styrene), poly)styrene-ethylene-butylene)*n,* polystyrene, polybutylene, poly (ethylene-propylene), poly(ethylene-butylene), polypropylene, or polyethylene, wherein said selected copolymer is a linear, branched, multiarm, or star shaped copolymer, *and n is a positive number.*

2. A composite article of claim 1, *5, 6, 7, 8, 9, 10, 11, 12, 13, 14, 15, 16, 17, 18, 19, 20, 21, 22, 23, 24, 25* wherein said article is a vibration damper, a vibration isolator, a wrapper, a hand exerciser, a dental floss, a crutch cushion, a cervical pillow, a bed wedge pillow, a leg rest cushion, a neck cushion, a mattress, a bed pad, an elbow pad, a dermal pad, a wheelchair cushion, a helmet liner, a hot or cold compress pad, an exercise weight belt, or a traction pad.

3. A composite article of claim 1, *5, 6, 7, 8, 9, 10, 11, 12, 13, 14, 15, 16, 17, 18, 19, 20, 21, 22, 23, 24, 25* wherein said article is a splint, sling, or [brice] *brace* cushion for the hand, wrist, finger, forearm, knee, leg, clavicle, shoulder, foot, ankle, neck, back, and rib or an orthopedic shoe sole.

4. A composite article formed from the composition of clam 1, *5, 6, 7, 8, 9, 10, 11, 12, 13, 14, 15, 16, 17, 18, 19, 20, 21, 22, 23, 24, 25* wherein said triblock copolymer is characterized by a Brookfield Viscosity of a 20 weight percent solids solution in toluene at 25° C. of substantially greater than 1,800 cps.

5. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed of the combination GnGnMn, GnGnGnMnGn, [GnMn,] GnMnGn, MnGnMn, MnMnGn, MnGnGnMn, GnMnGnMn, MnGnGnGn, MnMnMnGn, MnMnMnGnMnMnMn, MnGnMnMn, MnGnMnGn, GnMnGnGn, GnMnMnGn, GnGnMnMn, GnGnMnGnMn, GnMnGnMnMn, GnMnGnMnGn, GnMnMnGnGn, GnGnGnMnMn, MnGnGnMnGn, MnGnMnGnMn, GnGnMnMnMn, GnMnMnGnMn, MnGnMnGnMnGn, GnGnMnGnMnGn, *GnGnMnMnGn,* GnGnMnGnMnGn, GnMnGnMnGnMn, GnMnMnGnGnMn, MnGnGnMnGnMn, GnGnMnMnGnGn, *MnGnGnMnGnMn,* MnGnGnMnGnGn, GnGnMnGnGnMn, GnMnGnMnGnGn, MnGnMnGnMnGnMn, GnMnGnMnGnMnGn, GnMnMnGnMnMnGn, MnGnGnMnGnGnMn, MnGnMnGnMnGnMn, GnGnMnMnGnGnMnMn, GnGnMnGnGnMnGnGn, [MnGnGnMnGnGnMn,] GnMnGnGnMnGnGnMn, GnGnMnGnMnGnMnGnGn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented gel, a non-oriented gel, a tacky gel or a non-tacky gel; said triblock copolymer is a linear, multi-arm, branched, or star shaped copolymer of the general configuration poly(styrene-ethylene-butylene-styrene) in combination with a selected amount of poly(styrene-ethylene-propylene)n or poly(styrene-ethylene-butylene)n, wherein said selected copolymer is a linear, branched, multiarm, or star shaped copolymer, *wherein n of said copolymer is a positive number.*

6. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnGnMn, GnGnGnMnGn, [GnMn,] GnMnGn, MnGnMn, MnMnGn, MnGnGnMn, GnMnGnMn, MnGnGnGn, MnMnMnGn, MnMnMnGnMnMnMn, MnGnMnMn, MnGnMnGn, GnMnGnGn, GnMnMnGn, GnGnMnMn, GnGnMnGnMn, GnMnGnMnMn, GnMnGnMnGn, GnMnMnGnGn, GnGnGnMnMn, MnGnGnMnGn, MnGnMnGnMn, GnGnMnMnMn, GnMnMnGnMn, MnGnMnGnMnGn, GnGnMnGnMn, GnMnGnMnGnMn, MnGnGnMnGnMn, GnGnMnMnGnGn, MnMnGnGnMnMn, [MnGnGnMnGnMn,] MnGnGnMnGnGn, GnGnMnGnGnMn, MnGnMnGnGnMn, GnMnGnMnGnMnGn, MnGnMnGnMnMnGn, GnMnMnGnMnMnGn, MnGnGnMnGnGnMn, GnMnGnMnGnMnGnMn, GnGnMnMnGnGnMnMn, GnMnGnMnGnGnGnGn, GnMnGnGnMnGnGnMnGn, GnGnMnGnMnGnMnGn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented gel, a non-oriented gel, a tacky gel or a non-tacky gel; said triblock copolymer is a linear, multi-arm, branched, or star shaped copolymer of the general configuration poly(styrene-ethylene-propylene-styrene) in combination with a selected amount of poly(styrene-ethylene-propylene)n or poly (styrene-ethylene-butylene)n, wherein said selected copolymer is a linear, branched, multiarm, or star shaped copolymer, *wherein n of said copolymer is a positive number.*

7. A composite article comprising of a thermoplastic, heat formable and heat reversible gelatinous elastomer composition, G, *which is physically interlocked with a selected material M,* said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination [GnMn,] GnGnMn, GnGnGnMn, GnGnGnGnMn, GnGnGnGnGnMn, GnMnGn, GnMnGnGn, GnMnMnMnGn, MnGnMn, MnGnMnGnMn, MnMnGnMnMn, MnMnMnGnMnMnMn, MnMnMnGnMnGnMnMn, MnMnMnGnMnMnGnMnMn, MnMnMnMnGnMnGnMnMnMn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer is a linear, multi-arm, branched, or star shaped copolymer of the general configuration poly(styrene-ethylene-butylene-styrene), poly(styrene-ethylene-propylene-styrene) or a mixture thereof; *and optionally in combination with a selected amount of at elast one polymer or copolymer selected from the group consisting of poly (styrene-ethylene-propylene)n, poly(styrene-ethylene-butylene)n, polystyrene, polybutylene, poly(ethylene-propylene), poly(ethylene-butylene), polypropylene, or polyethylene, wherein said selected copolymer is linear, branched, multiarm, or star shaped copolymer and n is a positive number.*

8. A composite article comprising of a thermoplastic, heat formable and heat reversible gelatinous elastomer composition, G, *which is physically interlocked with a selected material M,* said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination [GnMn,] GnMnGn, GnMnGnMnGn, GnMnGnMnGnMnGn, GnMnGnMnGnMnGnMnGn, MnGnMn, MnMnGnMnMn, MnMnMnGnMnMnMn or any permutations of said combination, wherein when n is a subscript of M, n is the same or different selected from the group consisting of foam, plastic, fabric, metal, concrete, wood, glass, ceramics, synthetic resin, synthetic fiber or refractory materials; wherein when n is a subscript of G, n denotes the same or a different rigidity gel, an oriented (optically birefringent) gel, a non-oriented gel, a tacky gel or a non-tacky gel; said triblock copolymer is a linear, multi-arm, branched, or star shaped copolymer of the general configuration poly(styrene-ethylene-butylene-styrene), poly(styrene-ethylene-propylene-styrene) or a mixture thereof; *and optionally in combination with a selected amount of at least one polymer or copolymer selected from the group consisting of poly (styrene-ethylene-propylene), poly(ethylene-butylene), polypropylene, or polyethylene, wherein said selected copolymer is a linear, branched, multiarm, or star shaped copolymerand n is a positive number.*

9. *A composite article comprising of a thermoplastic, heat formable or heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-propylene-* styrene) or poly(styrene-ethylene-propylene)n, or a mixture of poly(styrene-ethylene-propylene-styrene) and poly(styrene-ethylene-butylene-styrene) or poly(styrene-ethylene-propylene)n and poly(styrene-ethylene-butylene-styrene); wherein n is a positive number.

10. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-propylene-styrene).

11. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-propylene)n; wherein n is a positive number.

12. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-butylene-styrene) in combination as a mixture with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)n, low viscosity poly(styrene-ethylene-propylene-styrene), low viscosity poly(styrene-ethylene-butylene-styrene), polystyrene, polybutylene, poly(ethylene-propylene), poly(ethylene-butylene), polypropylene, or polyethylene, wherein said selected copolymer is a linear, branched, multiarm, or star shaped copolymer; and wherein n is a positive number.

13. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-propylene-styrene) in combination as a mixture with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)n, low viscosity poly(styrene-ethylene-propylene-styrene), low viscosity poly(styrene-ethylene-butylene-styrene), poly(styrene-ethylene-butylene)n, polystyrene, polybutylene, poly(ethylene-propylene), poly(ethylene-butylene), polypropylene, or polyethylene, wherein said selected copolymer is a linear, branched, multiarm, or star shaped copolymer; and wherein n is a positive number.

14. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-propylene)n in combination as a mixture with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)n, low viscosity poly(styrene-ethylene-propylene-styrene), low viscosity poly(styrene-ethylene-butylene-styrene), poly(styrene-ethylene-butylene)n, polystyrene, polybutylene, poly(ethylene-propylene), poly(ethylene-butylene), polypropylene, or polyethylene, wherein said selected copolymer is a linear, branched, multiarm, or star shaped copolymer; and wherein n is a positive number.

15. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-propylene)n or as a mixture of poly(styrene-ethylene-propylene)n or poly(styrene-ethylene-butylene)n in combination with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)n, low viscosity poly(styrene-ethylene-propylene-styrene), low viscosity poly(styrene-ethylene-butylene-styrene), polystyrene, polybutylene, poly(ethylene-propylene), poly(ethylene-butylene), polypropylene, or polyethylene, wherein said selected copolymer is a linear, branched, multiarm, or star shaped copolymer; and wherein n is a positive number.

16. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-butylene-styrene) in combination as a mixture with a selected amount of low viscosity poly(styrene-ethylene-propylene-styrene) or low viscosity poly(styrene-ethylene-butylene-styrene).

17. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed in the combination GnMn, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-butylene-styrene) in combination as a mixture with a selected amount of low viscosity poly(styrene-ethylene-butylene-styrene).

18. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed of the combination GnMnGn, MnGnMn, GnGnMnGn, GnGnGnMnGnGn, MnMnGn, MnGnGnMn, GnMnGnMn, GnMnMnGn, GnMnMnMnGn, MnGnMnGnMn, MnMnGnMnMn, MnMnMnGn, MnGnMnMn, MnGnMnGn, GnMnGnGn, GnGnMnGn, GnGnMnGn, GnGnMnGnMn, GnMnGnMnMn, GnMnGnMnGn, GnMnMnGnGn, GnGnGnMnGn, MnGnGnMnMn, MnGnGnMnGn, GnGnMnMnMn, GnMnMnGnMn, MnGnMnGnMnGn, GnGnMnMnGn, GnGnMnGnMnGn, GnMnGnMnGnMn, GnMnMnGnGnMn, MnGnGnMnGnMn, GnGnMnMnGnGn, MnMnGnGnMnMn, MnMnGnMnGnMnMn, MnMnMnGnMnMn, MnGnMnGnMn, GnMnGnMnGnMnGn, MnGnMnGnMnMnGn, GnMnMnGnMnMnGn, GnMnMnGnMnGnMn, GnGnMnMnGnGnMnMn, GnGnMnGnGnMnGnGn, MnGnMnGnMnGnMn, GnMnGnMnGnMnGnMnGn, GnGnMnGnMnGnMnGnGn, MnMnGnMnGnMnMnMn, MnMnMnGnMnMnGnMnMnMn, MnMnMnGnMnMnGnMnMnMn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly (styrene-ethylene-butylene-styrene), poly(styrene-ethylene-propylene-styrene), poly(styrene-ethylene-butylene)n, poly (styrene-ethylene-propylene)n, or a mixture thereof; and said composition optionally in combination with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)n, low viscosity poly(styrene-ethylene-propylene-styrene), low viscosity poly(styrene-ethylene-butylene-styrene), poly (styrene-ethylene-butylene)n, polystyrene, polybutylene, poly(ethylene-propylene), poly(ethylene-butylene), polypropylene, or polyethylene, wherein said selected copolymer is a linear, branched, multiarm, or star shaped copolymer; wherein said n of said copolymer is a positive number.

19. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed of the combination GnMnGn, GnGnMn, MnGnMn, GnGnMnGn, GnGnGnMn, GnGnGnGnMn, GnGnGnGnGnMn, GnGnGnMnGnGn, MnMnGn, MnGnGnMn, GnMnGnMn, GnMnMnGn,
GnMnMnMnGn, MnGnMnGnMn, MnMnGnMnMn,
MnMnMnGn, MnGnMnMn, MnGnMnGn, GnMnGnGn,
GnGnMnMn, GnGnMnGnMn, GnMnGnMnMn,
GnMnGnMnGn, GnMnMnGnGn, GnGnGnMnMn,
MnGnGnMnGn, GnGnMnMnMn, GnMnMnGnMn,
MnGnMnGnMnGn, GnGnMnGnMn, GnGnMnGnMnGn,
G n M n G n M n G n M n,    G n M n M n G n G n M n,
M n G n G n M n G n M n,    G n G n M N M n G n G n,
M n M n G n G n M n M n,    M n G n G n M n G n M n,
M n G n G n M n G n G n,    G n G n M n G n G n M n,
M n M n M n G n M n M n M n,    M n G n M n G n G n M n,
GnMnGnMnGnMnGn, MnGnMnGnMnMnGn,
GnMnMnGnMnMnGn, GnMnGnMnGnMnGnMn,
GnGnMnMnGnGnMnMn, GnGnMnGnGnMnGnGn,
MnGnGnMnGnGnMn, GnMnGnGnMnGnGnMnGn,
GnGnMnGnMnGnMnGnGn, MnMnMnGnMnMnGnMnMnMn,
M n M n M n G n M n M n G n M n M n M n,
MnMnMnGnMnMnMnGnMnMnMn, or any permutations of
said combination, wherein when n is a subscript of M, n is
the same or different selected from the group consisting of
foam, plastic, fabric, metal, concrete, wood, glass, ceramics,
synthetic resin, synthetic fibers or refractory materials;
wherein when n is a subscript of G, n denotes a different
rigidity gel, an oriented (optically birefringent) gel, a non-
oriented gel, a tacky gel or a non-tacky gel; said triblock
copolymer being a linear, multi-arm, branched, or star
shaped coplymer of the general configuration poly(styrene-
ethylene-butylene-styrene), poly(styrene-ethylene-
propylene-styrene), or a mixture thereof; and said compo-
sition optionally in combination with a selected amount of at
least one polymer or copolymer selected from the group
consisting of poly(styrene-butadiene-styrene), poly(styrene-
butadiene), poly(styrene-isoprene-styrene), poly(styrene-
isoprene), poly(styrene-ethylene-propylene)n, low viscosity
poly(styrene-ethylene-propylene-styrene), low viscosity poly
(styrene-ethylene-butylene-styrene), poly(styrene-ethylene-
butylene)n, polystyrene, polybutylene, poly(ethylene-
propylene), poly(ethylene-butylene), polypropylene, or
polyethylene, wherein said selected copolymer is a linear,
branched, multiarm, or star shaped copolymer; wherein
said n of said copolymer is a positive number.

20. A composite article comprising of a thermoplastic,
heat formable and heat reversible gelatinous elastomer
composition, G, which is physically interlocked with a
selected material M, said gelatinous elastomer composition
formed from (a) 100 parts by weight of a high viscosity
triblock copolymer; (b) from about 300 to about 1,600 parts
by weight of a plasticizing oil; said composition character-
ized by a gel rigidity of from about 20 to about 800 gram
Bloom; said composite formed of the combination GnMnGn,
MnGnMn, GnGnMnGn, GnGnGnMnGnGn, MnMnGn,
MnGnGnMn, GnMnGnMn, GnMnMnGn, GnMnMnMnGn,
MnGnMnGnMn, MnMnGnMnMn, MnMnMnGn,
MnGnMnMn, MnGnMnGn, GnGnMnMn, GnGnMnGnMn,
GnGnMnGnMn, GnMnGnMnMn, GnMnGnMnGn,
GnMnMnGnGn, GnGnGnMnMn, MnGnMnMnGn,
GnGnMnMnMn, GnGnMnGnMnGn, GnMnGnMnGnMn,
G n M n G n M n G n G n M n,    M n G n G n M n G n M n,
G n G n M n G n G n,    M n G n G n M n G n M n,
MnGnGnMnGnMn, MnGnGnMnGnGn, GnMnGnGnMnGn,
M n M n M n G n M n M n M n,    M n G n M n G n G n M n,
G n M n G n M n G n M n G n,    M n G n M n G n M n M n G n,
GnMnMnGnMnMnGn, GnMnGnMnGnMnGnMn,
GnGnMnMnGnGnMnMn, GnGnMnGnGnMnGnGn,
MnGnGnMnGnGnMn, GnMnGnGnMnGnGnMnGn,
GnGnMnGnMnGnMnGnGn, MnMnMnGnMnGnMnMnMn,
M n M n M n G n M n M n G n M n M n M n, GnGnMnGnMnGnMnGnGn, MnMnMnGnMnGnMnMnMn,
M n M n M n G n M n M n G n M n M n M n,
MnMnMnGnMnMnMnGnMnMnMn, or any permutations of
said combination, wherein when n is a subscript of M, n is
the same or different selected from the group consisting of
foam, plastic, fabric, synthetic resin, or synthetic fibers;
wherein when n is a subscript of G, n denotes the same or
a different rigidity gel, an oriented (optically birefringent)
gel, a non-oriented gel, a tacky gel or a non-tacky gel; said
triblock copolymer being a linear, multi-arm, branched, or
star shaped copolymer of the general configuration poly
(styrene-ethylene-butylene-styrene), poly(styrene-ethylene-
propylene-styrene), or a mixture thereof; and said compo-
sition optionally in combination with a selected amount of at
least one polymer or copolymer selected from the group
consisting of poly(styrene-butadiene-styrene), poly(styrene-
butadiene), poly(styrene-isoprene-styrene), poly(styrene-
isoprene), poly(styrene-ethylene-propylene)n, low viscosity
poly(styrene-ethylene-propylene-styrene), low viscosity poly
(styrene-ethylene-butylene-styrene), poly(styrene-ethylene-
butylene)n, polystyrene, polybutylene, poly(ethylene-
propylene)poly(ethylene-butylene), polypropylene, or
polyethylene, wherein said selected copolymer is a linear,
branched, multiarm, or star shaped copolymer; wherein
said n of said copolymer is a positive number.

21. A composite article comprising of a thermoplastic,
heat formable and heat reversible gelatinous elastomer
composition, G, which is physically interlocked with a
selected material M, said gelatinous elastomer composition
formed from (a) 100 parts by weight of a high viscosity
triblock copolymer; (b) from about 300 to about 1,600 parts
by weight of a plasticizing oil; said composition character-
ized by a gel rigidity of from about 20 to about 800 gram
Bloom; said composite formed of the combination GnMnGn,
GnGnMn, MnGnMn, GnGnMnGn, GnGnGnMn,
GnGnGnGnMn, GnGnGnGnMn, GnGnGnMnGnGn,
MnMnGn, MnGnGnMn, GnMnGnMn, GnMnMnGn,
GnMnMnMnGn, MnGnMnGnMn, MnMnGnMnMn,
MnMnMnGn, MnGnMnMn, MnGnMnGn, GnMnGnGn,
GnGnMnMn, GnGnMnGnMn, GnMnGnMnMn,
GnMnGnMnGn, GnMnMnGnGn, GnGnGnMnMn,
MnGnMnMnGn, GnGnMnGnMn, GnMnGnMnGn,
GnMnGnMnGn, GnMnGnMnGn, GnGnGnMnGn,
MnGnMnGnMn, GnGnMnMnMn, GnMnMnGnMn,
MnGnMnGnMnGn, GnGnMnMnGn, GnGnMnGnMnGn,
G n M n G n M n G n M n,    G n M n M n G n G n M n,
M n G n G n M n G n M n,    G n G n M n M n G n G n,
M n M n G n G n M n M n,    M n G n G n M n G n M n,
M n G n G n M n G n G n,    G n G n M n G n G n M n,
M n M n M n G n M n M n M n,    M n G n M n G n G n M n,
GnMnGnMnGnMnGn, MnGnMnGnMnMnGn,
GnMnMnGnMnMnGn, GnMnGnMnGnMnGnMn,
GnGnMnMnGnGnMnMn, GnGnMnGnGnMnGnGn,
MnGnGnMnGnGnMn, GnMnGnGnMnGnGnMnGn,
GnGnMnGnMnGnMnGnGn, MnMnMnGnMnGnMnMnMn,
M n M n M n G n M n M n G n M n M n M n,
MnMnMnGnMnMnMnGnMnMnMn, or any permutations of
said combination, wherein when n is a subscript of M, n is
the same or different selected from the group consisting of
foam, plastic, fabric, synthetic resin, or synthetic fibers;
wherein when n is a subscript of G, n denotes a different
rigidity gel, an oriented (optically birefringent) gel, a non-
oriented gel, a tacky gel or a non-tacky gel; said triblock
copolymer being a linear, multi-arm, branched, or star
shaped copolymer of the general configuration poly(styrene-
ethylene-butylene-styrene), poly(styrene-ethylene-
propylene-styrene), or a mixture thereof; and said compo-
sition optionally in combination with a selected amount of at
least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)n, low viscosity poly(stryrene-ethylene-propylene-styrene), low viscosity poly(styrene-ethylene-butylene-styrene), poly(styrene-ethylene-butylene)n, polystyrene, polybutylene, poly(ethylene-propylene), poly(ethylene-butylene), polypropylene, or polyethylene, wherein said selected copolymer is a linear, branched, multiarm, or star shaped copolymer; wherein said n of said copolymer is a positive number.

22. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed of the combination GnMnGn, MnGnMn, GnGnMnGn, GnGnGnMnGnGn, MnMnGn, MnGnGnMn, GnMnGnMn, GnMnMnGn, GnMnMnMnGn, MnGnMnGnMn, MnMnGnMnMn, MnMnMnGn, MnGnMnMn, MnGnMnGn, GnMnGnGn, GnGnMnGn, GnGnMnGnMn, GnMnGnMnMn, GnMnGnMnGn, GnMnMnGnGn, GnGnGnMnMn, MnGnMnGnMn, GnGnMnMnMn, GnMnMnGnMn, MnGnMnGnMnGn, GnGnMnGnMnGn, GnMnGnMnGnMn, GnMnMnGnGnMn, MnGnGnMnGnMn, GnGnMnMnGnGn, GnGnMnGnGnMn, MnMnGnGnMnMn, MnGnMnGnMn, GnMnGnMnGnMnGn, MnGnMnGnMnMnGn, GnMnMnGnMnMnGn, GnMnGnMnGnMnGnMn, GnGnMnMnGnGnMnMn, GnGnMnGnGnMnGnGn, MnGnGnMnGnGnMn, GnMnGnMnGnGnMnGn, GnGnMnGnMnGnMnGnGn, MnMnMnGnMnMnGnMnMnMn, MnMnMnGnMnMnMnGnMnMnMn, or any permutations of said combination, wherein when n is a subscript of M, n is the same or different selected from the group consisting of plastic, fabric, synthetic resin, or synthetic fibers; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-butylene-styrene), poly(styrene-ethyelen-propylene-styrene), or a mixture thereof.

23. A composite article comprising of a thermoplastic, heat formable, and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed of the combination GnMnGn, GnGnMn, MnGnMn, GnGnMnGn, GnGnGnMn, GnGnGnGnMn, GnGnGnGnMn, GnGnGnMnGnGn, MnMnGn, MnGnGnMn, GnMnGnMn, GnMnMnGn, GnMnMnMnGn, MnGnGnMn, MnMnGnMnMn, MnMnMnGn, MnMnMnGn, MnGnMnMn, MnGnMnGn, GnMnGnGn, GnGnMnGn, GnGnMnGnMn, GnGnMnGnMn, GnMnGnMnMn, GnMnGnMnGn, GnMnMnGnGn, GnGnMnMn, MnGnGnMnGn, GnGnMnMnMn, GnMnMnGnMn, MnGnMnGnMnGn, GnGnMnGnMnGn, GnMnGnMnGnMn,
GnMnGnMnGnMn, GnMnMnGnGnMn,
MnGnGnMnGnMn, GnGnMnMnGnGn,
MnMnGnGnMnMn, MnGnGnMnGnMn,
MnGnMnGnMnGn, GnGnMnGnMnGn,
MnMnMnGnMnMnMn, MnGnMnGnMnGn,
GnMnGnMnGnMnGn, MnGnMnGnMnGn,
GnMnMnGnMnMnGn, GnMnGnMnGnMnGn,
GnGnMnMnGnGnMnMn, GnGnMnGnGnMnGnGn,
MnGnGnMnGnGnMn, GnMnGnMnGnGnMnGn,
GnGnMnGnMnGnMnGnGn, MnMnMnGnMnGnMnMnMn,
MnMnMnGnMnMnMnGnMnMnMn, or any permutations of said combination, wherein when n is a subscript of M, n is the same or different selected from the group consisting of plastic, fabric, synthetic resin, or synthetic fibers; wherein when n is a subscript of G, n denotes a different rigidity gel, an oriented (optically birefringent) gel, a non-oriented gel, a tacky gel and a non-tacky gel; said triblock copolymer being a linear, multi-arm, branched, or star shaped copolymer of the general configuration poly(styrene-ethylene-butylene-styrene), poly(styrene-ethylene-propylene-styrene), or a mixture thereof; when said composite is of the combination GnMn, said triblock copolymer is poly(styrene-ethylene-propylene-styrene), poly(styrene-ethylene-propylene)n or a mixture thereof or; (i) a mixture of poly(styrene-ethylene-butylene-styrene) and poly(styrene-ethylene-propylene)n or (ii) a mixture of poly(styrene-ethylene-butylene-styrene), poly(styrene-ethylene-propylene-styrene) and poly(styrene-ethylene-propylene)n, wherein said n of said copolymer is a positive number.

24. A composite article comprising a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed of the combination GnMnGn, MnGnMn, GnGnMnGn, GnGnGnMnGnGn, MnMnGn, MnGnGnMn, GnMnGnMn, GnMnMnGn, GnMnMnMnGn, MnGnMnGnMn, MnMnGnMnMn, MnMnMnGn, MnGnMnMn, MnGnMnGn, GnMnGnGn, GnGnMnGn, GnGnMnGnMn, GnMnGnMnMn, GnMnGnMnGn, GnMnMnGnGn, GnGnMnGnMn, GnGnGnMnMn, MnGnMnGnMn, GnGnMnMnMn, GnMnMnGnMn, GnGnMnMnMn, GnMnMnGnMn, MnGnMnGnMn, GnGnMnGnMn, GnMnGnMnGnMn, GnMnMnGnGnMn, MnGnGnMnGnMn, GnGnMnMnGnGn, MnMnGnGnMnMn, MnGnMnGnMn, GnMnGnMnGnMnGn, MnGnMnGnMnMnGn, GnMnMnGnMnMnGn, GnMnGnMnGnMnGn, GnGnMnMnGnGnMnMn, GnGnMnGnGnMnGnGn, MnGnGnMnGnGnMn, GnMnGnMnGnGnMnGn, GnGnMnGnMnGnMnGnGn, MnMnMnGnMnMnGnMnMnMn, MnMnMnGnMnMnMnGnMnMnMn, or any permutations of said combination, wherein when n is a subscript of M, n is the same or different selected from the group consisting of plastic, fabric, synthetic resin, or synthetic fibers; wherein when n is a subscript of G, n denotes the same or a different rigidity gel, an oriented (optically birefringent) gel, a non-oriented gel, a tacky gel or a non-tacky gel; said triblock copolymer being a linear, multi-arm, branched, or star shaped copolymer of the general configuration poly(styrene-ethylene-butylene-styrene), poly(styrene-ethylenepropylene-styrene), or a mixture thereof; when said composite is of the combination GnMn, said triblock copolymer is poly(styrene-ethylene-propylene-styrene) or a mixture of poly(styrene-ethylene-butylene-styrene) and poly(styrene-ethylene-propylene-styrene); and said composition optionally in combination with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)n, low viscosity poly(styrene-ethylene-propylene-styrene), low viscosity poly(styrene-ethylene-butylene-styrene), poly(styrene-ethylene-butylene)n, polystyrene, polybutylene, poly(ethylene-propylene), poly(ethylene-butylene), polypropylene, or polyethylene, wherein said selected copolymer is a linear, branched, multiarm, or star shaped copolymer, and said n is a positive number.

25. A composite article of claim 18, wherein said article is a dental floss, said composite formed of the combination GnMnGn, MnGnMn, MnGnGn, MnMnGn, or any permutations of said combination, wherein said material M is selected from the group consisting of plastic, synthetic resin, or synthetic fibers; said triblock copolymer being a linear, multi-arm, branched, or star shaped copolymer of the general configuration poly(styrene-ethylene-butylene-styrene), poly(styrene-ethylene-propylene-styrene), or a mixture thereof; when said composite is of the combination GnMn, said triblock copolymer is poly(styrene-ethylene-propylene-styrene) or a mixture of poly(styrene-ethylene-butylene-styrene) and poly(styrene-ethylene-propylene-styrene); and said composition optionally in combination with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)n, low viscosity poly(styrene-ethylene-propylene-styrene), low viscosity poly(styrene-ethylene-butylene-styrene), poly(styrene-ethylene-butylene)n, polystyrene, polybutylene, poly(ethylene-propylene), poly(ethylene-butylene), polypropylene, or polyethylene, wherein said selected copolymer is a linear, branched, multiarm, or star shaped copolymer, and said n is a positive number.

26. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed of the combination GnMn, GnMnGn, MnGnMn, GnGnMnGn, GnGnGnMnGnGn, MnMnGn, MnGnGnMn, GnMnGnMn, GnMnMnGn, GnMnMnMnGn, MnGnMnGnMn, MnMnGnMnMn, MnMnMnGn, MnGnMnMn, MnGnMnGn, GnMnGnGn, GnGnMnMn, GnGnMnGnMn, GnMnGnMnMn, GnMnGnMnGn, GnMnMnGnGn, GnGnMnMn, MnGnGnMnGn, GnMnMnMn, GnMnMnGnMn, MnGnMnMnGnMnMnGn, GnGnMnMnGn, GnGnMnGnMnGn,
GnMnGnMnGnMn, GnMnMnGnGnMn,
MnGnGnMnGnMn, GnGnMnMnGnGn,
MnMnGnGnMnMn, MnGnGnMnGnMn,
MnGnGnMnGnGn, GnGnMnGnGnMn,
MnMnMnGnMnMnMn, MnGnMnGnGnMn,
GnMnGnMnGnMnGn, MnGnMnGnMnMnGn,
GnMnMnGnMnMnGn, GnMnGnMnGnMnGnMn,
GnGnMnMnGnGnMnMn, GnGnMnGnMnGnMnGn, MnGnGnMnGnGnMn, GnMnGnGnMnGnGnMnGn,
GnGnMnGnMnGnMnGnGn, MnMnMnGnMnGnMnMnMn,
MnMnMnGnMnMnMnGnMnMnMn, or any permutations of said combination, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes an oriented (optically birefringent) gel or a non-tacky gel of the same or a different rigidity gel; said triblock copolymer being a linear, multi-arm, branched, or star shaped copolymer of the general configuration poly(styrene-ethylene-butylene-styrene), poly(styrene-ethylene-propylene-styrene), poly(styrene-ethylene-butylene)n, poly(styrene-ethylene-propylene)n, or a mixture thereof; and said composition optionally in combination with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)n, low viscosity poly(styrene-ethylene-propylene-styrene), low viscosity poly(styrene-ethylene-butylene-styrene), poly(styrene-ethylene-butylene)n, polystyrene, polybutylene, poly(ethylene-propylene), poly(ethylene-butylene), polypropylene, or polyethylene, wherein said selected copolymer is a linear, branched, multiarm, or star shaped copolymer; wherein said n of said copolymer is a positive number.

27. A composite article comprising of a thermoplastic, heat formable and heat reversible gelatinous elastomer composition, G, which is physically interlocked with a selected material M, said gelatinous elastomer composition formed from (a) 100 parts by weight of a high viscosity triblock copolymer; (b) from about 300 to about 1,600 parts by weight of a plasticizing oil; said composition characterized by a gel rigidity of from about 20 to about 800 gram Bloom; said composite formed of the combination GnMn, GnMnGn, GnGnMn, MnGnMn, GnGnMnGn, GnGnGnMn, GnGnGnGnMn, GnGnGnGnMnGn, GnGnGnMnGnGn, MnGnMnGn, MnGnGnMn, GnMnGnMn, GnMnMnGn, GnMnMnMnGn, MnGnMnGnMn, MnMnGnMnMn, MnMnMnGn, MnGnMnMn, MnGnMnGn, GnMnGnGn, GnGnMnMn, GnGnMnGnMn, GnMnGnMnMn, GnMnGnMnGn, GnMnMnGnGn, GnGnMnMn, MnGnGnMnGn, GnMnMnMn, GnMnMnGnMn, MnGnMnMnGnMnMnGn, GnGnMnMnGn, GnGnMnGnMnGn, MnGnMnGnMnGnMn, GnMnGnMnGnMnGn, GnMnGnMnGnMnGnMn, GnMnMnGnMnMnGn, GnGnMnGnMnGnMnGn, GnMnGnMnGnMnMnGn, MnGnGnMnGnGnMn, GnMnGnGnMnGnGnMnGn, GnGnMnGnMnGnMnGnGn, MnMnMnGnMnMnMnGnMnMnMn, MnMnMnGnMnMnMnGnMnMnMn, wherein when n is a subscript of M, n is the same or different selected from the group consisting of foam, plastic, fabric, metal, concrete, wood, glass, ceramics, synthetic resin, synthetic fibers or refractory materials; wherein when n is a subscript of G, n denotes an oriented (optically birefringent) gel or a non-tacky gel of the same or different rigidity gel; said triblock copolymer being a linear, multi-arm, branched, or star shaped copolymer of the general configuration poly(styrene-ethylene-butylene-styrene), poly(styrene-ethylenepropylene-styrene), poly(styrene-ethylene-butylene)n, poly(styrene-ethylene-propylene)n, or a mixture thereof; and said composition optionally in combination with a selected amount of at least one polymer or copolymer selected from the group consisting of poly(styrene-butadiene-styrene), poly(styrene-butadiene), poly(styrene-isoprene-styrene), poly(styrene-isoprene), poly(styrene-ethylene-propylene)n, low viscosity poly(styrene-ethylene-propylene-styrene), low viscosity poly(styrene-ethylene-butylene-styrene), poly(styrene-ethylene-butylene)n, polystyrene, polybutylene, poly(ethylene-propylene), poly(ethylene-butylene), polypropylene, or polyethylene, wherein said selected copolymer is a linear, branched, multiarm, or star shaped copolymer; wherein said n of said copolymer is a positive number.

* * * * *